United States Patent [19]

Higuchi et al.

[11] Patent Number: 5,395,824

[45] Date of Patent: Mar. 7, 1995

[54] DIPEPTIDE DERIVATIVE AND PROPHYLACTIC AND THERAPEUTIC AGENT FOR BONE DISEASES CONTAINING THE SAME

[75] Inventors: Naoki Higuchi, Kanagawa; Masayuki Saitoh, Osaka; Shinjiro Niwata, Osaka; Yoshinobu Kiso, Osaka; Yasuhiro Hayashi, Osaka, all of Japan

[73] Assignee: Suntory Limited, Osaka, Japan

[21] Appl. No.: 969,453

[22] Filed: Oct. 30, 1992

[30] Foreign Application Priority Data

Nov. 19, 1991 [JP] Japan .................. 3-303351

[51] Int. Cl.$^6$ .............................. A61K 37/02
[52] U.S. Cl. ..................... 514/19; 562/575; 562/559; 562/445; 562/444
[58] Field of Search ............ 514/17, 19; 530/330, 530/332; 562/575, 559, 445, 444

[56] References Cited

U.S. PATENT DOCUMENTS 5,081,284  1/1992  Higuchi et al. .................. 560/159

FOREIGN PATENT DOCUMENTS

| 0272671 | 6/1988 | European Pat. Off. ....... C07K 5/00 |
| 63-284127 | 11/1988 | Japan . |
| 1121257 | 5/1989 | Japan . |
| 2-218610 | 8/1990 | Japan . |
| 2-218663 | 8/1990 | Japan . |
| WO90/06919 | 6/1990 | WIPO . |
| WO92/12140 | 7/1992 | WIPO ................. C07D 265/30 |

OTHER PUBLICATIONS

J. Med. Chem., 1990, vol. 33, pp. 11–13, Communications to the Editor.
Y. Saito et al. "The structure-function . . . " Chemical Abstracts #46708h, vol. 115, No. 4, (5 Aug. 1991) Columbus, Ohio (USA).

(List continued on next page.)

*Primary Examiner*—Robert J. Hill, Jr.
*Assistant Examiner*—David Lukton
*Attorney, Agent, or Firm*—Nixon & Vanderhye

[57] ABSTRACT

A prophylactic or therapeutic agent for malignant hypercalcemia, bone Paget's disease and osteoporosis is disclosed, which contains as an active ingredient a dipeptide derivative represented by formula:

$$R^1NH-CH(R^2)-CO-NH-CH(R^3)-R^4 \quad (I)$$

wherein $R^1$ represents an aliphatic acyl group, a halogen-substituted aliphatic acyl group, or benzyloxycarbonyl group; $R^2$ represents a lower alkyl group or an aralkyl group; $R^3$ represents a lower alkyl group, an aralkyl group, or methylthioethyl group; $R^4$ represents formyl group, an aliphatic acyl group, an aliphatic acyl group substituted with a halogen atom or a lower alkoxycarbonyl group, a di-lower alkoxymethyl group, a diacyloxymethyl group, a lower alkoxalyl group, a 1-hydroxy-2-lower alkoxycarbonylethyl group, a halogen-substituted 1-hydroxy-2-lower alkoxycarbonylethyl group, hydroxyiminomethyl group, ureidoiminomethyl group, benzimidazol-2-yl group, or a group:

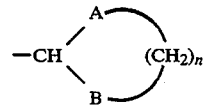

wherein A and B, which may be the same or different, each represents O, S, NH; and n represents 2 or 3; provided that $R^4$ is not a formyl group when $R^3$ is an n-butyl group.

10 Claims, No Drawings

OTHER PUBLICATIONS

N. Higuchi et al. "Cycteine proteinase inhibitors . . . " Chemical Abstracts #174674y, vol. 111, No. 19, (6 Nov. 1989) Columbus, Ohio (USA), p. 778.

B. Shimizu. "Peptides containing aromatic . . . " Chemical Abstracts #146554g, vol. 80, No. 25, (24 Jun. 1974), Columbus, Ohio (USA), p. 481.

I. J. Galbin et al. "Analogs of chymostatin" Chemical Abstracts #19717u, vol. 100, No. 3 (16 Jan. 1984), Columbus, Ohio (USA), p. 242.

B. Imperiali et al. "Inhibition of serine proteases . . . " Biochemistry, vol. 25, No. 13 (1986), Easton, Pa. (USA), pp. 3760–3767.

W. Steglich et al. "Uberfuhrung von N–acylaminosauren . . . " Tetrahedron Letters, vol. 22, No. 43 (1981), Oxford, GB, pp. 4263–4264.

J. M. Delaisse et al. "The effects of inhibitors of . . . " Bone, vol. 8 No. 5, (1987), New York, USA, pp. 305–313.

T. Sasaki et al. "Inhibitory effects of diand . . . " Journal of Enzyme Inhibition, vol. 3, No. 3 (1980), London, GB, pp. 195–201.

DIPEPTIDE DERIVATIVE AND PROPHYLACTIC AND THERAPEUTIC AGENT FOR BONE DISEASES CONTAINING THE SAME

BACKGROUND OF THE INVENTION

1. Field of the Invention

This invention relates to a novel dipeptide derivative and a prophylactic and therapeutic agent for bone diseases containing the same as an active ingredient.

2. Prior Art

In recent years, the rapid increase in the number of aged people in the population has caused an increase of so-called geriatric diseases. Among these diseases, bone diseases including osteoporosis are accompanied by a higher incidence of bone fracture, and this has been the major cause of the increase of aged patients who are bed-ridden. Therefore it is urgently required to develop a method for preventing and treating the above-mentioned bone diseases.

Bone is not a tissue which does not undergo any change once formed. It is continuously formed and metabolized. Thus the structure and amount of bone is maintained due to the balance between osteogenesis and bone resorption. When this balance is lost due to aging or some other factors, various bone diseases are induced. Examples of diseases due to sthenic bone resorption include malignant hypercalcemia caused by myeloma or lymphoma, bone Paget's disease caused by local bone resorption and osteoporosis in aged people accompanied by decrease in bone weight, though the etiological causes of this disease are as yet unknown.

Bones mainly comprise collagen fibers (i.e., organic matter) and calcium salts (i.e., inorganic matter). These substances are combined to form bones, constructions which are highly resistant against tension and pressure. In particular, calcium salts amount to 70% of the total bone weight. As bone diseases proceed, calcium salts tend to dissolve into the blood and thus are slowly lost.

Known methods for preventing or treating these diseases comprise supplying calcium or maintaining the normal calcium level, and in this context active vitamin D3 preparations and calcium preparations have been employed. Further, hormone preparations, such as estrogen preparations and calcitonin preparations, have been used in order to suppress decalcification of bones.

In addition to the above-mentioned therapeutic methods for preventing a decrease of calcium salts, importance of preventing a decrease of collagen fibers in bone diseases has been recently noted. Namely, studies have been conducted to elucidate enzymes decomposing collagen fiber present as a matrix of bones in an attempt to develop an inhibitor of such enzymes for use in the treatment of bone resorption diseases (see Japanese Patent Laid-Open Nos. 284127/1988 and 218619/1990). However, these studies have just been initiated, and it is only but yesterday that collagen type I, which is the collagen contained in bones as the matrix, was found to be decomposed by cathepsin L which is a thiol protease found among lysosomal enzymes [see Nobuhiko Katsunuma, Gakushikai Kaiho, No. 792, 48–53 (1991)]. No clinical cases where patients were cured by using an inhibitor of a collagen decomposing enzyme have been reported, and no practical therapeutic agent of this type has been provided so far.

SUMMARY OF THE INVENTION

An object of the present invention is to provide a compound useful for prevention or treatment of bone resorption diseases, such as malignant hypercalcemia, bone Paget's disease, and osteoporosis, and a treating agent containing the same as an active ingredient.

More specifically, the object of the present invention is to provide a novel compound effective in suppressing a decrease of calcium salts in bones and an agent containing the same as an active ingredient for drastically preventing and treating bone diseases in place of the conventional therapy comprising supplying calcium or maintaining a calcium level.

Another object of the present invention is to provide a treating agent for bone diseases which enables more effective prevention and treatment of bone resorption diseases by simultaneously suppressing the decrease of collagen Fibers and calcium salts in bones.

DETAILED DESCRIPTION OF THE INVENTION

The present inventors previously found that a cathepsin L inhibitor has an activity to decrease the blood calcium concentration in mouse models of hypercalcemia induced by a 1–34 amino acid fragment of parathyroid hormone-related protein [hereinafter abbreviated as PTHrp(1–34 sequence ID No. 1)] and is effective in bone resorption diseases [see Seikagaku, 63, (8), 824 (1991)].

The inventors have further conducted extensive investigations to find more effective compounds by using rat models of PTHrp(1–34)-induced hypercalcemia [*Journal of Clinical Investigation*, 81, (2), 596–600 (1988) and *Endocrinology*, 123, 2841–2848 (1988)]. As a result, it has now been found that a dipeptide derivative represented by formula (I):

$$R^1NH\text{---}CH(R^2)\text{---}CO\text{---}NH\text{---}CH(R^3)\text{---}R^4 \qquad (I)$$

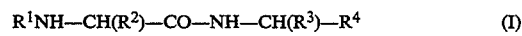

wherein $R^1$ represents a halogen-substituted or unsubstituted aliphatic acyl group or benzyloxycarbonyl group; $R^2$ represents a lower alkyl group or an aralkyl group; $R^3$ represents a lower alkyl group, an aralkyl group, or methylthioethyl group; $R^4$ represents formyl group, an aliphatic acyl group, an aliphatic acyl group substituted with halogen atom or a lower alkoxycarbonyl group, a di-lower alkoxymethyl group, a diacyloxymethyl group, a lower alkoxalyl group, a halogen-substituted or unsubstituted 1-hydroxy-2-lower alkoxycarbonylethyl group, hydroxyiminomethyl group, ureidoiminomethyl group, benzimidazol-2-yl group, or a group:

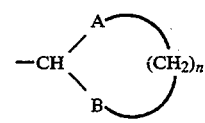

wherein A and B, which may be the same or different, each represents O, S, NH; and n represents 2 or 3; provided that $R^4$ is not formyl group when $R^3$ is n-butyl group, decreases blood calcium concentration when administered orally or parenterally, for example, intraperitoneally or intravenously, and thus is useful as a prophylactic or therapeutic agent for bone diseases. The present invention has been completed based on this finding.

The present invention also provides a prophylactic or therapeutic agent for bone diseases containing at least one of the compounds represented by formula (I) as an active ingredient.

The bone diseases which may be treated with the therapeutic agent of the present invention are bone resorption diseases, such as malignant hypercalcemia, bone Paget's disease, and osteoporosis.

The terminology "lower alkyl group" as used herein means a straight or branched alkyl group having from 1 to 5 carbon atoms, e.g., methyl, ethyl, propyl, isopropyl, n-butyl, isobutyl, and sec-butyl groups.

In formula (I), the halogen-substituted or unsubstituted aliphatic acyl group as represented by $R^1$ preferably includes acetyl group, chloroacetyl group, propionyl group, butyryl group, isobutyryl group, and trifluoroacetyl group. Preferred examples of the lower alkyl group as represented by $R^2$ include isopropyl group, n-butyl group, isobutyl group, and sec-butyl group, with isobutyl group being particularly preferred. Preferred examples of the aralkyl group as represented by $R^2$ include benzyl group.

Preferred examples of the lower alkyl group as represented by $R^3$ include isopropyl group, n-butyl group, isobutyl group, and sec-butyl group, with n-butyl group being particularly preferred. The aralkyl group as $R^3$ preferably includes benzyl group.

The aliphatic acyl group which may be substituted with a halogen atom or a lower alkoxycarbonyl group as represented by $R^4$ preferably includes acetyl group, bromoacetyl group, and 2-ethoxycarbonylacetyl group. The di-lower alkoxymethyl group as $R^4$ preferably includes dimethoxymethyl group, diethoxymethyl group, and di-n-propyloxymethyl group. The diacyloxymethyl group as $R^4$ preferably includes diacetoxymethyl group. The di-lower alkoxalyl group as $R^4$ preferably includes ethoxalyl group. The halogen-substituted or unsubstituted 1-hydroxy-2-lower alkoxycarbonylethyl group as $R^4$ preferably includes 1-hydroxy-2-ethoxycarbonylethyl group and 1-hydroxy-2,2-difluoro-2-ethoxycarbonylethyl group.

The group: 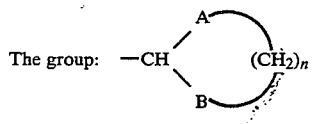

as represented by $R^4$ preferably includes 1,3-dioxolan-2-yl group, 1,3-dithiolan-2-yl group, 1,3-dithian-2-yl group, thiazolidine-2-yl group, and 1,3-oxothiolan-2-yl group.

The dipeptide derivatives according to the present invention can be prepared through Processes A to F described below.

Process A:

The compounds of formula (I) wherein $R^1$ is benzyloxycarbonyl group (hereinafter referred to as Z) and $R^4$ is —CO—COOR$^5$ (wherein $R^5$ represents a lower alkyl group) are prepared by saponifying a compound represented by formula (II):

$$R^1-NH-CO(R^2)-CO-NH-CH(R^3)-COOR^6 \quad (II)$$

wherein $R^1$, $R^2$ and $R^3$ are as defined above; and $R^6$ represents a lower alkyl group, in an alkaline aqueous solution, converting the resulting carboxylic acid to an acid anhydride, reacting the acid anhydride first with methoxymethylamine and then with ethyl vinyl ether, and finally oxidizing the compound with ozone.

Process B:

The compounds of formula (I) wherein $R^1$ is Z and $R^4$ is —CO—R$^7$ represents methyl group or a halogenated methyl group) are prepared by saponifying the compound represented by formula (II) in an alkaline aqueous solution, converting the resulting carboxylic acid to an acid anhydride, diazomethylating the acid anhydride, and reacting the product with a hydrogen halide.

Process C:

The compounds of formula (I) wherein $R^1$ is Z and $R^4$ is —CO—CH$_2$—COOR$^8$ (wherein $R^8$ represents a lower alkyl group) are prepared by saponifying the compound represented by formula (II) in an alkaline aqueous solution, imidazoylating the resulting carboxylic acid, and reacting the product with an acetate ester.

Process D:

The compounds of formula (I) wherein $R^1$ is Z and $R^4$ is —CH(OH)—CX$_2$—COOR$^8$ (wherein $R^8$ represents a lower alkyl group; and X represents hydrogen atom or a halogen atom) are prepared by reducing the compound represented by formula (II) with a reducing agent, e.g., sodium borohydride, in an organic solvent, e.g., a lower alcohol or an ether, to give an alcohol compound, reacting the alcohol compound with an oxidizing agent, e.g., sulfur trioxide-pyridine complex, chromic anhydride-pyridine complex, or oxalyl chloride, in an organic solvent in the presence or absence of a tertiary amine to obtain a compound represented by formula (III):

$$Z-NH-CH(R^2)-CO-NH-CH(R^3)-CHO \quad (III)$$

wherein $R^2$ and $R^3$ are as defined in formula (I) above, and reacting the compound of formula (III) with an acetate ester.

The compound of formula (III) may also be obtained by reducing the compound of formula (II) in an organic solvent by using a diisobutylaluminum hydride.

Process E:

The compounds of formula (I) wherein $R^1$ is Z and $R^4$ is a di-lower alkoxymethyl group, a diacyloxymethyl group, a lower alkoxalyl group, hydroxyiminomethyl group, ureidoiminomethyl group, benzimidazol-2-yl group, or a group:

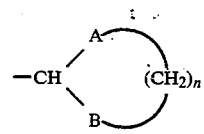

(wherein A, B, and n are as defined above) are prepared by reacting the compound represented by formula (III) with an alcohol, an acylating agent (e.g., an acid anhydride or an acid halide), hydroxylamine, semicarbazide, o-phenylenediamine, a diol, a dithiol, or an aminothiol.

Process F:

The compounds of formula (I) wherein $R^1$ is a halogen-substituted or unsubstituted aliphatic acyl group and $R^4$ is a di-lower alkoxymethyl group, a diacyloxymethyl group, a lower alkoxalyl group, hydroxyiminomethyl group, ureidoiminomethyl group, benzimidazol-2-yl group or a group:

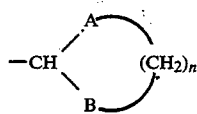

(wherein A, B, and n are as defined above) are prepared by reacting a compound represented by formula (IV):

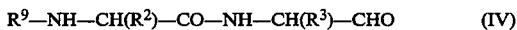

wherein $R^2$ and $R^3$ are as defined in formula (I) above; and $R^9$ represents a conventional peptide protective group, such as benzyloxycarbonyl group, with an alcohol, an acylating agent (e.g., an acid anhydride or an acid halide), hydroxylamine, semicarbazide, o-phenylenediamine, a diol, a dithiol, or an aminothiol to obtain a compound represented by formula (V):

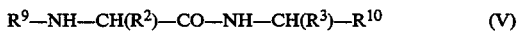

wherein $R^2$, $R^3$, and $R^9$ are as defined above; and $R^{10}$ represents a di-lower alkoxymethyl group, a diacyloxymethyl group, a lower alkoxalyl group, hydroxyiminomethyl group, ureidoiminomethyl group, benzimidazol-2-yl group, or a group:

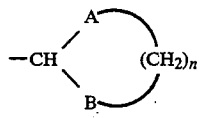

(wherein A, B, and n are as defined above), removing the protective group $R^9$ by, for example, catalytic hydrogenation, and introducing a desired acyl group $R^1$ to the deprotected amino group by using a corresponding acid anhydride or acid halide.

The compound of formula (V) may also be obtained by reacting a compound represented by formula (VI):

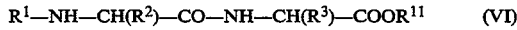

wherein $R^1$ represents a halogen-substituted or unsubstituted aliphatic acyl group; $R^2$ and $R^3$ are as defined in formula (I) above; and $R^{11}$ represents a lower alkyl group, with the similar reducing agent and oxidizing agent as used in the preparation of the compound of formula (III) to obtain a compound represented by formula (VII):

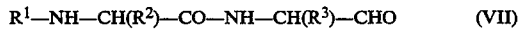

wherein $R^1$, $R^2$, and $R^3$ are as defined in formula (VI) above, and reacting the resulting compound with an alcohol, an acylating agent (e.g., an acid anhydride or an acid halide), hydroxylamine, semicarbazide, o-phenylenediamine, a diol, a dithiol, or an aminothiol.

The active ingredient may be administered in the form of various preparations produced in a conventional manner. Examples of oral preparations include capsules, tablets, granules, fine granules, syrups, and dry syrups. Examples of parenteral preparations include injections, suppositories (such as rectal or vaginal suppositories), nasal preparations (such as sprays), and percutaneous preparations (such as ointments and percutaneous absorption tapes).

The active ingredient is generally administered either orally or parenterally in a dose of from 1 to 1000 mg/kg, preferably from 1 to 100 mg/kg/day, and more preferably from 5 to 50 mg/kg/day, for adults in a single dose or 2 or 3 divided doses. The dose may be varied depending on the age and condition of each patient.

The active ingredient of the present invention is capable of normalizing blood calcium concentration in rat models of hypercalcemia induced by PTHrp(1-34). PTHrp is the protein identified as a factor responsible for inducing human hypercalcemia, and PTHrp(1-34) is an active fragment consisting of the 1st to 34th amino acid residues of PTHrp. PTHrp(1-34) promotes in vitro bone resorption and, when administered to rats, induces hypercalcemia. It is thus useful for obtaining an osteoporosis model due to its bone resorption promoting activity in vitro [*Journal of Clinical Investigation*, 81, (2), 596-600 (1988) and *Endocrinology*, 123, 2841-2848 (1988)].

The compound of the present invention was administered to Wistar rats, PTHrp(1-34) was then given to the animals, and the blood calcium concentration was measured 1 hour after the administration. As a result, it was found that test groups showed a significantly reduced blood calcium concentration as compared with the control group which received PTHrp(1-34) alone. That is, the compounds of the present invention suppress hypercalcemia induced by PTHrp(1-34) and are therefore useful as a prophylactic or therapeutic agent for bone diseases.

The present invention is now illustrated in greater detail with reference to Examples, Test Examples, and Formulation Examples, but it should be understood that the present invention is not construed as being limited thereto. All the parts and percents are by weight unless otherwise indicated.

EXAMPLE 1

Preparation of N-Benzyloxycarbonyl-L-leueine-(1-ethoxalyl)pentylamide a) Preparation of N-Benzyloxycarbonyl-L-leueyl-L-norleucine Methyl Ester:

In 200 ml of dimethylformamide (DMF) was dissolved 26.5 g of N-benzyloxycarbonyl-L-leucine, and 19.2 g of 1-ethyl-3-(3-diethylaminopropyl)carbodiimide hydrochloride was added thereto. To the solution were added 18.2 g of L-norleueine methyl esther hydrochloride and 10.1 g of triethylamine, followed by stirring at room temperature for 12 hours. After completion of the reaction, water was added to the teaetlon mixture. The mixture was extracted with ethyl acetate, and the extract was washed successively with a 10% citric acid solution, a saturated brine, a sodium bicarbonate solution, and a saturated brine, and dried over magnesium sulfate. The solvent was removed by distillation under reduced pressure, and the residue was purified by medium-pressure column chromatography on silica gel to obtain 22.0 g of the titled compound as a colorless crystal.

b) Preparation of N-Benzyloxycarbonyl-L-leueyl-L-norleucine:

In 120 ml of methanol was dissolved 7.0 g of the N-benzyloxycarbonyl-L-leueyl-L-norleucine methyl ester as obtained in (a) above, and 20 ml of a 1N sodium hydroxide aqueous solution was added thereto, followed by stirring at 60° C. for 1 hour. After completion of the reaction, the solvent was removed by distillation, and the residue was dissolved in water. The aqueous layer was washed with diethyl ether, made acidic with 1N hydrochloric acid, and the precipitated crystal was collected by filtration to obtain 6.8 g of the titled compound as a colorless crystal. c) Preparation of N-Benzyloxycarbonyl-L-leucyl-L-norleucine-(N-methyl-N-methoxy)amide:

In 100 ml of methylene chloride were dissolved 4.1 g of N-benzyloxycarbonyl-L-leucyl-L-norleucine obtained in (b) above and 2.0 g of N-methylmorpholine. The solution was cooled to −15° C., and 1.0 g of ethyl chloroformate was added thereto, followed by stirring at −15° C. for 40 minutes. To the reaction mixture was added 1.5 g of methoxymethylamine hydrochloride, and the mixture was stirred at −15° C. for 30 minutes and then at room temperature for 12 hours. After completion of the reaction, the reaction mixture was poured into excess water and extracted with ethyl acetate. The extract was washed successively wiEh 1N hydrochloric acid, a saturated brine, a saturated sodium bicarbonate solution, and a saturated brine, and dried over magnesium sulfate. The solvent was removed by distillation under reduced pressure, and the residue was purified by medium-pressure column chromatography on silica gel to obtain 4.4 g of the titled compound as a colorless crystal.

d) Preparation of N-Benzyloxycarbonyl-L-leucine-[1-(1-oxo-2-ethoxy)vinyl]pentylamide:

To 100 ml of anhydrous tetrahydrofuran (THF) was added 10.3 ml of ethyl vinyl ether. After cooling the solution to −78° C., 42 ml of a 1.4M pentane solution of t-butyl lithium was added thereto dropwise. The temperature of the reaction mixture was gradually raised up to 0° C. over 1 hour, and the mixture was stirred at that temperature for 1 hour. The reaction mixture was cooled to −30° C., and a solution of 15.1 g of magnesium bromide ethyl etherate in 100 ml of anhydrous THF was added thereto. The temperature of the reaction mixture was gradually raised up to 0° C. over 15 minutes, and the mixture was stirred at that temperature for 1 hour. To the reaction mixture was added a solution of 5.8 g of N-benzyloxycarbonyl-L-leucyl-L-norleucine-(N-methyl-N-methoxy)amide obtained in (c) above in 50 ml of anhydrous THF, the temperature of the reaction mixture was elevated up to room temperature, and the mixture was stirred at that temperature for 2 hours. The reaction mixture was poured into a dilute aqueous solution of ammonium chloride and extracted with ethyl acetate. The organic layer was washed successively with a saturated sodium hydrogencarbonate aqueous solution and a saturated brine and dried over magnesium sulfate. The solvent was removed by distillation under reduced pressure, and the residue was purified by medium-pressure column chromatography on silica gel to obtain 2.5 g of the titled compound as an oily substance.

e) Preparation of N-Benzyloxycarbonyl-L-leucine-(1-ethoxalyl)pentylamide:

In 150 ml of dry methylene chloride were dissolved 2.5 g of N-benzyloxycarbonyl-L-leucine-[1-(1-oxo-2-ethoxy)vinyl]pentylamide and 1.0 ml of pyridine, and the solution was cooled to −78° C. Ozone gas was bubbled into the solution until the mixture became blue. After completion of the reaction, the excess ozone was driven out by introducing oxygen gas, and 1.0 ml of dimethyl sulfide and 1.0 ml of pyridine were added to the reaction mixture, followed by stirring for 3 minutes. The reaction mixture was warmed to room temperature, and the organic layer was washed with water and dried over anhydrous magnesium sulfate. The solvent was removed by distillation under reduced pressure, and the residue was purified by medium-pressure column chromatography on silica gel to obtain 2.2 g of the titled compound as an oily substance.

EXAMPLE 2

Preparation of N-benzyloxycarbonyl-L-leucine-(1-acetyl)pentylamide a) Preparation of N-Benzyloxycarbonyl-L-leucyl-(1-diazomethylacetyl)pentylamide:

In 150 g of anhydrous THF were dissolved 5.4 g of N-benzyloxycarbonyl-L-leucyl-L-norleucine prepared in the same manner as in Example 1-(b) and 3.4 ml of N-methylmorpholine, and 1.6 g of ethyl chloroformate was added thereto under ice-cooling, followed by stirring at 0° C. for 30 minutes. The reaction mixture was added to an excess diazomethane solution in diethyl ether, and the solution was allowed to stand at 0° C. for 1 hour. The solvent was removed by distillation under reduced pressure, and the residue was purified by medium-pressure column chromatography on silica gel to obtain 4.0 g of the titled compound as a colorless crystal.

b) Preparation of N-Benzyloxycarbonyl-L-leucine-(1-acetyl)pentylamide:

In dry methylene chloride was dissolved 600 mg of N-benzyloxycarbonyl-L-leucyl-(1-diazomethylacetyl)-pentylamide obtained in (a) above, and 0.6 ml of 55% hydrogen iodide was added thereto, followed by stirring at 0° C. for 20 minutes. After completion of the reaction, the solvent was removed by distillation under reduced pressure, and the residue was purified by medium-pressure column chromatography on silica gel to obtain 300 mg of the titled compound as a colorless crystal.

EXAMPLE 3

Preparation of N-Benzyloxycarbonyl-L-leucine-[1-(1-bromoacetyl)-]pentylamide

In dry methylene chloride was dissolved 600 mg of N-benzyloxycarbonyl-L-leucyl-(1-diazomethylacetyl)-pentylamide obtained in the same manner as in Example 2-(a), and 0.5 ml of 47% hydrogen bromide was added thereto, followed by stirring at 0° C. for 30 minutes. After completion of the reaction, the solvent was removed under reduced pressure, and the residue was purified by medium-pressure column chromatography on silica gel to obtain 600 mg of the titled compound as a colorless crystal.

EXAMPLE 4

Preparation of N-Benzyloxycarbonyl-L-leucine-[1-(1-hydroxy-2,2-difluoro-2-ethoxycarbonylethyl)]pentylamide a) Preparation of N-Benzyloxycarbonyl-L-leucine-(1-hydroxymethyl)pentylamide:

In 200 ml of t-butanol were suspended 8.0 g of N-benzyloxycarbonyl-L-leucyl-L-norleucine methyl ester obtained in the same manner as in Example 1-(a) and 2.4 g of sodium borohydride, and the suspension was refluxed at 90° C. in a nitrogen atmosphere. Then, 32 ml of absolute methanol was added dropwise to the reaction mixture under refluxing. After the addition, the mixture was further refluxed with stirring for 30 minutes. The reaction mixture was allowed to cool to room temperature, and 100 ml of water was added thereto under cooling with ice. The methanol and t-butanol were removed by distillation under reduced pressure, and the residue was extracted three times with ethyl acetate. The extract was washed with a saturated brine and dried over anhydrous sodium sulfate. The solvent was removed by distillation, and the residue was purified by medium-pressure column chromatography on silica gel to obtain 4.4 g of the titled compound as a colorless crystal.

b) Preparation of N-Benzyloxycarbonyl-L-leucine-(1-formyl)pentylamide:

In 24 ml of anhydrous dimethyl sulfoxide (DMSO) were dissolved 3.4 g of N-benzyloxycarbonyl-L-leucine-(1-hydroxymethyl)pentylamide prepared in (a) above and 3.6 g of triethylamine, and a solution of 6.0 g of a sulfur trioxide-pyridine complex in 24 ml of anhydrous DMSO was added thereto, followed by stirring at room temperature for 10 minutes. The reaction mixture was poured into 200 ml of ice-water and extracted three times with ethyl acetate. The extract was washed successively with a 10% citric acid solution, a saturated brine, a saturated sodium bicarbonate solution, and a saturated brine and dried over anhydrous sodium sulfate. The solvent was removed by distillation under reduced pressure. The residue was recrystallized from a mixed solvent of ethyl acetate and hexane to give 2.4 g of the titled compound as a colorless crystal.

c) Preparation of N-Benzyloxycarbonyl-L-leucine-[1-(1-hydroxy-2,2-difluoro-2-ethoxycarbonylethyl)]pentylamide:

To 8.0 ml of anhydrous THF was added 500 mg of zinc powder, and the mixture was heated at reflux. To the mixture was added dropwise a solution of 0.8 ml of ethyl bromodifluoroacetate in 6.0 ml of anhydrous THF, followed by heating at reflux for 5 minutes. A solution of 1.0 g of N-benzyloxycarbonyl-L-leucine-(1-formyl)pentylamide obtained in (b) above in 10 ml of anhydrous THF was then added thereto dropwise, and the mixture was heated at reflux for 10 minutes. After allowing to cool, a saturated sodium bicarbonate solution was added to the reaction mixture, and the mixture was extracted with ethyl acetate. The organic layer was washed with water, dried over anhydrous sodium sulfate, and distilled under reduced pressure to remove the solvent. The residue was purified by medium-pressure column chromatography on silica gel to obtain 470 mg of the titled compound as an oily substance.

EXAMPLE 5

Preparation of N-Benzyloxycarbonyl-L-leucine-[1-(1-hydroxy-2-ethoxycarbonylethyl)]pentylamide To 10 ml of anhydrous THF were added 360 mg of zinc powder and a small amount of iodide, and the mixture was heated at reflux. A solution of 0.54 ml of ethyl bromoacetate in 6.0 ml of anhydrous THF was added thereto dropwise, followed by heating at reflux for 5 minutes. A solution of 1.0 g of N-benzyloxycarbonyl-L-leucine-(1-formyl)pentylamide prepared in the same manner as in Example 4-(b) in 14 ml of anhydrous benzene was then added thereto dropwise, followed by heating at reflux for 30 minutes. After allowing the mixture to cool, 1N hydrochloric acid was added thereto, and the reaction mixture was extracted with ethyl acetate. The organic layer was washed with water and dried over anhydrous sodium sulfate. The solvent was removed by distillation under reduced pressure, and the residue was purified by medium-pressure column chromatography on silica gel to obtain 410 mg of the titled compound as an oily substance.

EXAMPLE 6

Preparation of N-Benzyloxycarbonyl-L-leucine-[1-(2-ethoxycarbonylacetyl)]pentylamide In 10 ml of anhydrous THF was dissolved 1.3 g of N-benzyloxycarbonyl-L-leucyl-L-norleucine prepared in the same manner as in Example 1-(b), and 680 mg of carbodiimidazole was added thereto, followed by refluxing for 2 hours. The reaction mixture was cooled to $-78°$ C., and 6.1 ml of a 2M lithium diisopropylamide solution in hexane and 1.05 ml of anhydrous ethyl acetate were added thereto, followed by stirring for 30 minutes. After completion of the reaction, the reaction mixture was poured into a saturated ammonium chloride aqueous solution and extracted with ethyl acetate. The organic layer was washed with a saturated brine and dried over anhydrous sodium sulfate. The solvent was removed by distillation under reduced pressure. The residue was purified by medium-pressure column chromatography on silica gel to obtain 540 mg of the titled compound as a yellow solid.

EXAMPLE 7

Preparation of N-Benzyloxycarbonyl-L-leucine-(1-dimethoxymethyl)pentylamide

In 10 ml of methanol was dissolved 820 mg of N-benzyloxycarbonyl-L-leucine-(1-formyl)pentylamide obtained in the same manner as in Example 4-(b), and a catalytic amount of p-toluenesulfonic acid was added thereto, followed by stirring at room temperature for 4 hours. After completion of the reaction, the reaction mixture was partitioned between water and ethyl acetate. The organic layer was washed with a saturated brine and dried over anhydrous sodium sulfate. The solvent was removed by distillation under reduced pressure. The residue was purified by medium-pressure column chromatography on silica gel to obtain 910 mg of the titled compound as a colorless crystal.

EXAMPLE 8

Preparation of N-Benzyloxycarbonyl-L-leucine-(1-ureidoiminomethyl)pentylamide

In 10 ml of ethanol was dissolved 850 mg of N-benzyloxycarbonyl-L-leucine-(1-formyl)pentylamide obtained in the same manner as in Example 4-(b), and 2 ml of water and 1.0 g of semicarbazide hydrochloride were added thereto, followed by stirring at room temperature for 2 hours. After completion of the reaction, the solvent was removed by distillation under reduced pressure. The residue was purified by medium-pressure column chromatography on silica gel to obtain 900 mg of the titled compound as a colorless crystal.

EXAMPLE 9

Preparation of N-Benzyloxycarbonyl-L-leucine-1-(1,3-dioxolan2-yl)]pentylamide

In 10 ml of benzene was dissolved 500 mg of N-benzyloxycarbonyl-L-leucine-(1-formyl)pentylamide obtained in the same manner as in Example 4-(b), and 0.9 ml of ethylene glycol and a catalytic amount of p-toluenesulfonic acid were added thereto, followed by heating at reflux for 2 hours. After completion of the reaction, the reaction mixture was poured into a saturated sodium bicarbonate solution, and the organic layer was washed with a saturated brine and dried over anhydrous sodium sulfate. The solvent was removed by distillation under reduced pressure. The residue was purified by medium-pressure column chromatography on silica gel to obtain 380 mg of the titled compound as a colorless crystal.

EXAMPLE 10

Preparation of
N-Benzyloxycarbonyl-L-leucine-[1-(benzimidazol-2-yl)]pentylamide

In 20 ml of methanol was dissolved 1.1 g of N-benzyloxycarbonyl-L-leucine-(1-formyl)pentylamide obtained in the same manner as in Example 4-(b), and 356 mg of o-phenylenediamine and 0.2 ml of a 50% aqueous solution of acetic acid were added thereto. The mixture was allowed to react at room temperature for 40 hours. After completion of the reaction, the solvent was removed by distillation under reduced pressure. The residue was purified by medium-pressure column chromatography on silica gel to obtain 330 mg of the titled compound as a colorless crystal.

EXAMPLE 11

Preparation of
N-Benzyloxycarbonyl-L-leucine-(1-hydroxyiminomethyl)pentylamide

In 15 ml of ethanol was dissolved 1.0 g of N-benzyloxycarbonyl-L-leucine-(1-formyl)pentylamide obtained in the same manner as in Example 4-(b), and 210 mg of hydroxyammonium chloride and 5 ml of pyridine were added thereto. The mixture was allowed to react at room temperature for 24 hours. After completion of the reaction, the solvent was removed by distillation under reduced pressure, and the residue was purified by medium-pressure column chromatography on silica gel to obtain 830 mg of the titled compound as a colorless crystal.

EXAMPLE 12

Preparation of
N-Benzyloxycarbonyl-L-leucine-(1-diacetoxymethyl)-pentylamide

In 10 ml of acetic anhydride was dissolved 1.0 g of N-Benzyloxycarbonyl-leucine-(1-formyl)pentylamide obtained in the same manner as in Example 4-(b), and 0.84 ml of boron trifluoride ethyl etherate was added thereto. The mixture was allowed to rear at room temperature for 3 hours. After completion of the reaction, the solvent was removed by distillation under reduced pressure. The residue was purified by medium-pressure column chromatography on silica gel to obtain 300 mg of the titled compound as an oily substance.

EXAMPLE 13

Preparation of N-Benzyloxycarbonyl-L-leucine-[1-(1,3-dithiolan-2-yl)]pentylamide In 20 ml of anhydrous methylene chloride was dissolved 1.0 g of N-benzyloxycarbonyl-L-leucine-(1-formyl)pentylamide obtained in the same manner as in Example 4-(b), and 300 mg of 1,2-ethanedithiol and 0.8 ml of boron trifluoride ethyl etherate were added thereto. The mixture was allowed to react at room temperature for 12 hours. After completion of the reaction, the solvent was removed by distillation under reduced pressure, and the residue was purified by medium-pressure column chromatography on silica gel to obtain 900 mg of the titled compound as a colorless crystal.

EXAMPLE 14

Preparation of N-Benzyloxycarbonyl-L-leucine-[1-(1,3-dithian-2-yl)]pentylamide

In 20 ml of anhydrous methylene chloride was dissolved 1.0 g of N-benzyloxycarbonyl-L-leucine-(1-formyl)pentylamide obtained in the same manner as in Example 4-(b), and 300 mg of 1,3-propanedithiol and 0.8 ml of boron trifluoride ethyl etherate were added thereto. The mixture was allowed to react at room temperature for 12 hours. After completion of the reaction, the solvent was removed by distillation under reduced pressure, and the residue was purified by medium-pressure column chromatography on silica gel to obtain 900 mg of the titled compound as a colorless crystal.

EXAMPLE 15

Preparation of
N-Benzyloxycarbonyl-L-leucine-[1-(thiazolidine-2-yl)]pentylamide

In 20 ml of methanol was dissolved 1.0 g of N-benzyloxycarbonyl-L-leucine-(1-formyl)pentylamide obtained in the same manner as in Example 4-(b), and 400 mg of 2-aminoethanethiol hydrochloride, 0.4 ml of triethylamine, and a catalytic amount of concentrated sulfuric acid were added thereto. The mixture was allowed to react at room temperature for 12 hours. After completion of the reaction, the solvent was removed by distillation under redueed pressure. The residue was purified by medium-pressure column chromatography on silica gel to obtain 1.2 g of the titled compound as a colorless crystal.

EXAMPLE 16

Preparation of
N-Acetyl-L-leucine-(1-dimethoxymethyl)pentylamide a) Preparation of N-Acetyl-L-leucyl-L-norleucine Methyl Ester:

In 200 ml of ethanol was dissolved 8.0 g of N-benzyloxycarbonyl-L-leucyl-L-norleucine methyl ester obtained in the same manner as in Example 1-(a), and a catalytic amount of palladium-on-carbon was added thereto, followed by hydrogenation at room temperature for 12 hours in a hydrogen atmosphere. After completion of the reaction, the catalyst was removed by filtration, and the solvent was removed by distillation under reduced pressure. The residue was dissolved in pyridine, and 5 ml of acetic anhydride was added thereto, followed by stirring at room temperature for 12 hours. The reaction mixture was partitioned between water and ethyl acetate. The organic layer was washed successively with a 10% citric acid solution, a saturated brine, a saturated sodium bicarbonate solution, and a saturated brine, and dried over magnesium sulfate. The solvent was removed by distillation under reduced pressure, and the residue was purified by medium-pressure column chromatography on silica gel to obtain 5.0 g of the titled compound as a colorless crystal.

b) Preparation of N-Acetyl-L-leucine-(1-hydroxymethyl)pentylamide:

In 30 ml of t-butanol were suspended 1.7 g of N-acetyl-L-leucyl-L-norleucine methyl ester obtained in (a) above and 200 mg of sodium borohydride, and the suspension was refluxed at 90° C. in a nitrogen atmosphere. Then, 2 ml of absolute methanol was added thereto dropwise while refluxing. After the addition, the mixture was stirred at reflux for 30 minutes, followed by cooling to room temperature. To the reaction mixture was added 100 ml of water under cooling with ice, and the methanol and t-butanol were removed by distillation under reduced pressure. The residue was extracted three times with ethyl acetate, and the extract was washed with a saturated brine and dried over anhydrous sodium sulfate. The solvent was removed by distillation under reduced pressure, and the residue was purified by medium-pressure column chromatography on silica gel to obtain 900 mg of the titled compound as a colorless crystal.

c) Preparation of N-Acetyl-L-leucine-(1-formyl)pentylamide:

In 15 ml of anhydrous DMSO were dissolved 900 mg of N-acetyl-L-leucine-(1-hydroxymethyl)pentylamide obtained in (b) above and 1.8 ml of triethylamine, and a solution of 2.1 g of a sulfur trioxide-pyridine complex in 10 ml of anhydrous DMSO was added thereto while stirring. After the stirring was further continued at room temperature for 10 minutes, the reaction mixture was poured into 200 ml of ice-water and extracted with ethyl acetate three times. The extract was washed successively with a 10% citric acid solution, a saturated brine, a saturated sodium bicarbonate solution, and a saturated brine, and dried over anhydrous sodium sulfate. The solvent was removed by distillation under reduced pressure, and the residue was purified by medium-pressure column chromatography on silica gel to obtain 300 mg of the titled compound as an oily substance.

d) Preparation of N-Acetyl-L-leucine-(1-dimethoxymethyl)pentylamide:

In 20 ml of methanol was dissolved 750 mg of N-acetyl-L-leucine-(1-formyl)pentylamide obtained in (c) above, and a catalytic amount of p-toluenesulfonic acid was added thereto. The mixture was allowed to the mixture to react at room temperature for 5 hours. After completion of the reaction, the solvent was removed by distillation under reduced pressure, and the residue was purified by medium-pressure column chromatography on silica gel to obtain 800 mg of the titled compound as a colorless crystal.

EXAMPLE 17

Preparation of N-Acetyl-L-leucine-[1-(1,3-dioxolan-2-yl)]pentylamide

In 20 ml of benzene was dissolved 750 mg of N-acetyl-L-leucine-(1-formyl)pentylamide obtained in the same manner as in Example 16-(c), and 1.8 ml of ethylene glycol and a catalytic amount of p-toluenesulfonic acid were added thereto. The mixture was heated at reflux for 3.5 hours. After completion of the reaction, the solvent was removed by distillation under reduced pressure, and the residue was purified by medium-pressure column chromatography on silica gel to obtain 650 mg of the titled compound as a colorless crystal.

EXAMPLE 18

Preparation of N-Acetyl-L-leucine-(1-hydroxyiminomethyl)pentylamide

In 30 ml of ethanol was dissolved 750 mg of N-acetyl-L-leucine-(1-formyl)pentylamide obtained in the same manner as in Example 16-(c), and 210 mg of hydroxyammonium chloride and 5 ml of pyridine were added thereto. The mixture was allowed to react at room temperature for 24 hours. After completion of the reaction, the reaction mixture was washed with a saturated brine and dried over anhydrous sodium sulfate. The solvent was removed by distillation under reduced pressure, and the residue was purified by mediumpressure column chromatography on silica gel to obtain 600 mg of the titled compound as a colorless crystal.

EXAMPLE 19

Preparation of N-Acetyl-L-leucine-(1-ureidoiminomethyl)pentylamide

In 20 ml of ethanol was dissolved 750 mg of N-acetyl-L-leucine-(1-formyl)pentylamide obtained in the same manner as in Example 16-(c), and 1.5 g of sodium acetate, 1.0 g of semicarbazide hydrochloride, and 1 ml of water were added thereto. The mixture was allowed to react at room temperature for 24 hours. After completion of the reaction, the reaction mixture was washed with a saturated brine and dried over anhydrous sodium sulfate. The solvent was removed by distillation under reduced pressure, and the residue was purified by medium-pressure column chromatography on silica gel to obtain 550 mg of the titled compound as a colorless crystal.

EXAMPLE 20

Preparation of N-Acetyl-L-leucine-[1-(1,3-dithiolan-2-yl)]pentylamide

In 20 ml of methylene chloride was dissolved 1.8 g of N-acetyl-L-leucine-(1-formyl)pentylamide obtained in the same manner as in Example 16-(c), and 700 mg of 1,2-ethanedithiol and 1.5 ml of boron trifluoride ethyl etherate were added thereto. The mixture was allowed to react at room temperature for 12 hours. After completion of the reaction, the solvent was removed by distillation under reduced pressure, and the residue was purified by medium-pressure column chromatography on silica gel to obtain 1.7 g of the titled compound as a colorless crystal.

EXAMPLE 21

Preparation of N-Acetyl-L-leucine-[1-(thiazolidine-2-yl)]pentylamide

In 20 ml of methanol was dissolved 2.0 g of N-acetyl-L-leucine-(1-formyl)pentylamide obtained in the same manner as in Example 16-(c), and 800 mg of 2-aminoethanethiol, 1.0 ml of triethylamine, and a catalytic amount of concentrated sulfuric acid were added thereto. The mixture was allowed to react at room temperature for 12 hours. After completion of the reaction, the solvent was removed by distillation under reduced pressure, and the residue was purified by medium-pressure column chromatography on silica gel to obtain 1.8 g of the titled compound as a colorless crystal.

EXAMPLE 22

Preparation of
N-Acetyl-L-leucine-(1-diethoxymethyl)pentylamide

In 20 ml of ethanol was dissolved 1.8 g of N-acetyl-L-leucine-(1-formyl)pentylamide obtained in the same manner as in Example 16-(c), and a catalytic amount of p-toluenesulfonic acid was added thereto. The mixture was allowed to react at room temperature for 12 hours. After completion of the reaction, the solvent was removed by distillation under reduced pressure, and the residue was purified by medium-pressure column chromatography on silica gel to obtain 1.7 g of the titled compound as a colorless crystal.

EXAMPLE 23

Preparation of
N-Isobutyryl-L-leucine-(1-dimethoxymethyl)pentylamide a) Preparation of L-Leucine-(1-dimethoxymethyl)pentylamide:

In 30 ml of ethanol was dissolved 1.0 g of N-benzyloxycarbonyl-L-leucine-(1-dimethoxymethyl)pentylamide obtained in the same manner as in Example 7, and a catalytic amount of palladium-on-carbon was added thereto. The hydrogenation was conducted at room temperature for 12 hours in a hydrogen atmosphere. After completion of the reaction, the catalyst was removed by filtration, and the solvent was removed by distillation under reduced pressure to yield 650 mg of the titled compound as a colorless crystal.

b) Preparation of N-Isobutyryl-L-leucine-(1-dimethoxymethyl)-pentylamide:

In 10 ml of methylene chloride were dissolved 450 mg of L-leucine-(1-dimethoxymethyl)pentylamide obtained in (a) above and 360 mg of triethylamine, and the solution was cooled to 0° C. A solution of 190 mg of isobutyryl chloride in 5.0 ml of methylene chloride was added thereto dropwise, and the reaction was allowed to continue at room temperature for 90 minutes. After completion of the reaction, the organic layer was washed successively with water and a saturated brine and dried over anhydrous sodium sulfate. The solvent was removed by distillation under reduced pressure, and the residue was purified by medium-pressure column chromatography on silica gel to obtain 230 mg of the titled compound as a colorless crystal.

EXAMPLE 24

Preparation of
N-Chloroacetyl-L-leucine-(1-dimethoxymethyl)pentylamide

In 10 ml of methylene chloride were dissolved 450 mg of L-leucine-(1-dimethoxymethyl)pentylamide obtained in the same manner as in Example 23-(a) and 500 mg of triethylamine, and the solution was cooled to 0° C. A solution of 200 mg of chloroacetyl chloride in 5.0 ml of methylene chloride was then added thereto dropwise, and the reaction was allowed to continue at room temperature for 30 minutes. After completion of the reaction, the organic layer was washed successively with water and a saturated brine and dried over anhydrous sodium sulfate. The solvent was removed by distillation under reduced pressure, and the residue was purified by medium-pressure column chromatography on silica gel to obtain 360 mg of the titled compound as a colorless crystal.

EXAMPLE 25

Preparation of
N-Propionyl-L-leucine-(1-dimethoxymethyl)pentylamide

In 5 ml of methylene chloride were dissolved 450 mg of L-leucine-(1-dimethoxymethyl)pentylamide obtained in the same manner as in Example 23-(a) and 800 mg of triethylamine, and the solution was cooled to 0° C. A solution of 150 mg of propionyl chloride in 5.0 ml of methylene chloride was then added thereto dropwise, and the mixture was allowed to react at room temperature for 10 minutes. After completion of the reaction, the organic layer was washed successively with water and a saturated brine and dried over anhydrous sodium sulfate. The solvent was removed by distillation under reduced pressure, and the residue was purified by medium-pressure column chromatography on silica gel to obtain 400 mg of the titled compound as a colorless crystal.

EXAMPLE 26

Preparation of
N-Butyryl-L-leucine-(1-dimethoxymethyl)pentylamide

In 5 ml of methylene chloride were dissolved 450 mg of L-leucine-(1-dimethoxymethyl)pentylamide obtained in the same manner as in Example 23-(a) and 800 mg of triethylamine, and the solution was cooled to 0° C. A solution of 150 mg of butyryl chloride in 5.0 ml of methylene chloride was added thereto dropwise, and the mixture was allowed to react at room temperature for 1 hour. After completion of the reaction, the organic layer was washed successively with water and a saturated brine and dried over anhydrous sodium sulfate. The solvent was removed by distillation under reduced pressure, and the residue was purified by medium-pressure column chromatography on silica gel to obtain 400 mg of the titled compound as a colorless crystal.

EXAMPLE 27

Preparation of
N-Trifluoroacetyl-L-leucine-(1-dimethoxymethyl)pentylamide

In 50 ml of DMF were dissolved 1.2 g of L-leucine-(1-dimethoxymethyl)pentylamide obtained in the same manner as in Example 23-(a) and 470 mg of triethylamine, and the solution was cooled to 0° C. To the solution was added 890 mg of thioethyl trifluoroacetate, and the mixture was allowed to react at room temperature for 24 hours. After completion of the reaction, the reaction mixture was poured into water and extracted with diethyl ether. The organic layer was washed with a saturated brine and dried over anhydrous sodium sulfate. The solvent was removed by distillation under reduced pressure, and the residue was purified by medium-pressure column chromatography on silica gel to obtain 1.1 g of the titled compound as a colorless crystal.

EXAMPLE 28

Preparation of
N-Acetyl-L-leucine-[1-(1,3-oxothiolan-2-yl)]pentylamide

In 30 ml of dry benzene was dissolved 1.0 g of N-acetyl-L-leucine-(1-formyl)pentylamide obtained in the same manner as in Example 16-(c), and a catalytic amount of p-toluenesulfonic acid and 300 mg of mercaptoethanol were added thereto. The mixture was heated at reflux with stirring for 1 hour. After cooling to room temperature, the reaction mixture was partitioned between water and ethyl acetate. The organic layer was distilled under reduced pressure to remove the solvent, and the residue was purified by medium-pressure column chromatography to obtain 520 mg of the titled compound as a colorless crystal.

EXAMPLE 29

Preparation of
N-Acetyl-L-leucine-(1-formyl)phenethylamide a) Preparation of N-Acetyl-L-leucyl-L-phenylalanine Methyl Ester:

In 100 ml of DMF was dissolved 5.0 g of L-phenylalanine methyl ester hydrochloride, and 2.4 g of N-methylmorpholine was added thereto. To the solution were added 4.0 g of N-acetyl-L-leucine, 5.0 g of 1-hydroxybenzotriazole, and 5.5 g of 1-ethyl-3-(3-diethylaminopropyl)carbodiimide hydrochloride, and the mixture was stirred at room temperature for 24 hours. After completion of the reaction, water was added to the reaction mixture, and the mixture was extracted with ethyl acetate. The extract was washed successively with a 10% citric acid solution, a saturated brine, a saturated sodium bicarbonate solution, and a saturated brine and dried over sodium sulfate. The solvent was removed by distillation under reduced pressure, and the residue was purified by medium-pressure column chromatography on silica gel to obtain 6.7 g of the titled compound as a colorless crystal.

b) Preparation of N-Acetyl-L-leucine-(1-hydroxymethyl)phenethylamide:

In 100 ml of t-butanol were suspended 6.7 g of N-acetyl-L-leucine-L-phenylalanine methyl ester obtained in (a) above and 560 mg of sodium borohydride, and the suspension was refluxed at 90° C. in a nitrogen atmosphere. To the mixture was added dropwise 6 ml of absolute methanol while refluxing. The mixture was further stirred at reflux for 1 hour, and then cooled to room temperature. To the reaction mixture was added 300 ml of water under cooling with ice. The methanol and t-butanol were removed by distillation under reduced pressure, and the residue was extracted three times with ethyl acetate. The extract was washed with a saturated brine and dried over anhydrous sodium sulfate. The solvent was removed by distillation under reduced pressure, and the residue was purified by medium-pressure column chromatography on silica gel to obtain 6.1 g of the titled compound as an oily substance.

c) Preparation of N-Acetyl-L-leucine-(1-formyl)phenethylamide:

In 70 ml of anhydrous DMSO were dissolved 6.1 g of N-acetyl-L-leucine-(1-hydroxymethyl)phenethylamide obtained in (b) above and 17 ml of triethylamine, and a solution of 8.3 g of a sulfur trioxide-pyridine complex in 20 ml of anhydrous DMSO was added thereto. After stirring at room temperature for 45 minutes, the reaction mixture was poured into 300 ml of ice water and extracted three times with ethyl acetate. The extract was washed successively with a 10% citric acid solution, a saturated brine, a saturated sodium bicarbonate solution, and a saturated brine and dried over anhydrous sodium sulfate. The solvent was removed by distillation under reduced pressure, and the residue was purified by medium-pressure column chromatography on silica gel to obtain 4.0 g of the titled compound as a colorless crystal.

EXAMPLE 30

Preparation of
N-Acetyl-L-leucine-(1-dimethoxymethyl)phenethylamide

In 20 ml of methanol was dissolved 900 mg of N-acetyl-L-leucine-(1-formyl)phenethylamide obtained in the same manner as in Example 29, and a catalytic amount of p-toluenesulfonic acid was added thereto. The mixture was stirred at room temperature for 3 hours. After completion of the reaction, the solvent was removed by distillation under reduced pressure, and the residue was partitioned between an water and ethyl acetate. The organic layer was washed successively with a saturated sodium bicarbonate solution and a saturated brine and dried over anhydrous sodium sulfate. The solvent was removed by distillation under reduced pressure, and the residue was purified by medium-pressure column chromatography on silica gel to obtain 850 mg of the titled compound as a colorless crystal.

EXAMPLE 31

Preparation of
N-Acetyl-L-leucine-(1-formyl-3-methylthio)propylamide a) Preparation of N-Acetyl-L-leucyl-L-methionine Methyl Ester:

In 100 ml of DMF was dissolved 6.0 g of L-methionine methyl ester hydrochloride, and 3.3 ml of N-methylmorpholine was added thereto. To the solution were further added 5.2 g of N-acetyl-L-leucine, 4.6 g of 1-hydroxybenzotriazole, and 5.8 g of 1-ethyl-3-(3-diethylaminopropyl)carbodiimide hydrochloride, and the mixture was stirred at room temperature for 24 hours. After completion of the reaction, water was added to the reaction mixture, and the mixture was extracted with ethyl acetate. The extract was washed successively with a 10% citric acid solution, a saturated brine, a saturated sodium bicarbonate solution, and a saturated brine an dried over sodium sulfate. The solvent was removed by distillation under reduced pressure, and the residue was purified by medium-pressure column chromatography on silica gel to obtain 6.2 g of the titled compound as a colorless crystal.

b) Preparation of N-Acetyl-L-leucine-(1-hydroxymethyl-3-methylthio)propylamide:

In 50 ml of t-butanol were suspended 6.2 g of N-acetyl-L-leucine-L-methionine methyl ester obtained in (a) above and 780 mg of sodium borohydride, and the suspension was refluxed at 90° C. in a nitrogen atmosphere. To the solution was added dropwise 10 ml of absolute methanol while refluxing, followed by further refluxing with stirring for 1 hour. After cooling to room temperature, 100 ml of water was added to the reaction mixture under cooling with ice, and the methanol and t-butanol were removed by distillation under reduced pressure. The residue was extracted three times with ethyl acetate. The extract was washed with a saturated brine and dried over anhydrous sodium sulfate. The solvent was removed by distillation under reduced pressure, and the residue was recrystallized from a mixed solvent of methanol and ethyl acetate to obtain 2.4 g of the titled compound as a colorless crystal.

c) Preparation of N-Acetyl-L-leucine-(1-formyl-3-methylthio)propylamide:

In 20 ml of anhydrous DMSO were dissolved 1.4 g of N-acetyl-L-leucine-1-hydroxymethyl-3-methylthio)-propylamide obtained in (b) above and 2.1 ml of triethylamine, and a solution of 2.3 g of a sulfur trioxide-pyridine complex in 10 ml of anhydrous DMSO was added to the solution while stirring. After the stirring was continued at room temperature for 10 minutes, the reaction mixture was poured into 100 ml of ice water and extracted three times with ethyl acetate. The extract was washed successively with a 10% citric acid solution, a saturated brine, a saturated sodium bicarbonate solution, and a saturated brine and dried over anhydrous sodium sulfate. The solvent was removed by distillation under reduced pressure, and the residue was purified by medium-pressure column chromatography on silica gel to obtain 0.6 g the titled compound as an oily substance.

EXAMPLE 32

Preparation of N-Acetyl-L-leucine-(1-dimethoxymethyl-3-methylthio)propylamide

In 30 ml of methanol was dissolved 2.0 g of N-acetyl-L-leucine-(1-formyl-3-methylthio)propylamide obtained in the same manner as in Example 31, and a catalytic amount of p-toluenesulfonic acid was added thereto. The mixture was stirred at room temperature for 3 hours. After completion of the reaction, the methanol was removed by distillation under reduced pressure, and the residue was partitioned between water and ethyl acetate. The organic layer was washed with a saturated sodium bicarbonate solution and then with a saturated brine and dried over anhydrous sodium sulfate. The solvent was removed by distillation under reduced pressure, and the residue was purified by medium-pressure column chromatography on silica gel to obtain 2.1 g of the titled compound as a colorless crystal.

EXAMPLE 33

Preparation of N-Benzyloxycarbonyl-L-leucine-(1-formyl-3-methyl)-butylamide a) Preparation of N-Benzyloxycarbonyl-L-leucyl-L-leucine Methyl Ester:

In 30 ml of methylene chloride was dissolved 5.5 g of L-leucine methyl ester hydrochloride, and 4.2 ml of triethylamine was added thereto. To the solution were further added 8.0 g of N-benzyloxycarbonyl-L-leucine and 5.8 g of 1-ethyl-3-(3-diethylaminopropyl)carbodiimide hydrochloride, and the mixture was stirred at room temperature for 24 hours. After completion of the reaction, water was added, and the reaction mixture was extracted with ethyl acetate. The extract was washed successively with a 10% citric acid solution, a saturated brine, a saturated sodium bicarbonate solution, and a saturated brine and dried over sodium sulfate. The solvent was removed by distillation under reduced pressure, and the residue was purified by medium-pressure column chromatography on silica gel to obtain 9.2 g of the titled compound as a colorless crystal.

b) Preparation of N-Benzyloxycarbonyl-L-leucine-(1-hydroxymethyl-3-methyl)butylamide:

In 100 ml of t-butanol were suspended 9.2 g of N-benzyloxycarbonyl-L-leucine-L-leucine methyl ester obtained in (a) above and 900 mg of sodium borohydride, and the suspension was refluxed at 90° C. in a nitrogen atmosphere. Then, 20 ml of absolute methanol was added thereto dropwise while refluxing. After the addition, the refluxing with stirring was further continued for 1 hour. After cooling to room temperature, 300 ml of water was added under ice-cooling, the methanol and t-butanol removed by distillation under reduced pressure, and the mixture extracted three times with ethyl acetate. The extract was washed with a saturated brine and dried over anhydrous sodium sulfate. The solvent was removed by distillation under reduced pressure, and the residue was purified by medium-pressure column chromatography on silica gel to obtain 3.0 g of the titled compound as a colorless crystal.

c) Preparation of N-Benzyloxycarbonyl-L-leucine-(1-formyl-3-methyl)butylamide:

In 20 ml of anhydrous DMSO were dissolved 2.8 g of N-benzyloxycarbonyl-L-leucine-(1-hydroxymethyl-3-methyl)butylamide obtained in (b) above and 3.1 ml of triethylamine, and a solution of 3.7 g of a sulfur trioxidepyridine complex in 10 ml of anhydrous DMSO was added thereto while stirring. After stirring at room temperature for 10 minutes, the reaction mixture was poured into 100 ml of ice water and extracted with ethyl acetate three times. The extract was washed successively with a 10% citric acid solution, a saturated brine, a saturated sodium bicarbonate solution, and a saturated brine and dried over anhydrous sodium sulfate. The solvent was removed by distillation under reduced pressure, and the residue was crystallized from a mixed solvent of ethyl acetate and hexane to obtain 2.2 g of the titled compound as a colorless crystal.

EXAMPLE 34

Preparation of N-Acetyl-L-leucine-(1-dimethoxymethyl-3-methyl)-butylamide a) Preparation of N-Benzyloxycarbonyl-L-leucine-(1-dimethoxymethyl-3-methyl)butylamide:

In 50 ml of methanol was dissolved 1.4 g of N-benzyloxycarbonyl-L-leucine-(1-formyl-3-methyl)butylamide obtained in the same manner as in Example 33, and a catalytic amount of p-toluenesulfonic acid was added to the solution, followed by stirring at room temperature for 2 hours. After completion of the reaction, the solvent was removed by distillation under reduced pressure, and the residue was partitioned between water layer and ethyl acetate. The organic layer was washed successively with a saturated sodium bicarbonate solution and a saturated brine and dried over anhydrous sodium sulfate. The solvent was removed by distillation under reduced pressure, and the residue was purified by medium-pressure column chromatography on silica gel to obtain 1.5 g of the titled compound as a colorless crystal.

b) Preparation of N-Acetyl-L-leucine-(1-dimethoxymethyl-3-methyl)butylamide:

In 30 ml of ethanol was dissolved 1.5 g of N-benzyloxycarbonyl-L-leucine-(1-dimethoxymethyl-3-methyl)butylamide obtained in (a) above, and a catalytic amount of palladium-on-carbon was added thereto. The mixture was allowed to react at room temperature for 12 hours in a hydrogen atmosphere. After completion of the hydrogenation reaction, the catalyst was removed by filtration, and the solvent was removed by distillation under reduced pressure. The residue was dissolved in 50 ml of methylene chloride, and 9 ml of pyridine and 3 ml of acetic anhydride were added to the solution, followed by stirring at room temperature for 4 hours. Water was added to the reaction mixture, and the organic layer was washed successively with a 10% citric acid solution, a saturated brine, a saturated sodium bicarbonate solution, and a saturated brine and dried over anhydrous sodium sulfate. The solvent was removed by distillation under reduced pressure, and the residue was crystallized from a mixed solvent of ethyl acetate and hexane to obtain 930 ml of the titled compound as a colorless crystal.

EXAMPLE 35

Preparation of N-Benzyloxycarbonyl-L-leucine-(1-formyl-2-methyl)-butylamide a) Preparation of N-Benzyloxycarbonyl-L-leucyl-L-isoleucine Methyl Ester:

In 30 ml of methylene chloride was dissolved 5.5 g of L-isoleucine methyl ester hydrochloride, and 4.2 ml of triethylamine was added thereto. To the solution were further added 8.0 g of N-benzyloxycarbonyl-L-leucine and 5.8 g of 1-ethyl-3-(3-diethylaminopropyl)carbodiimide hydrochloride, followed by stirring at room temperature for 24 hours. After completion of the reaction, water was added, and the mixture was extracted with ethyl acetate. The extract was washed successively with a 10% citric acid solution, a saturated brine, a saturated sodium bicarbonate solution, and a saturated brine and dried over sodium sulfate, and the solvent was removed by distillation under reduced pressure. The residue was purified by medium-pressure column chromatography on silica gel to obtain 9.4 g of the titled compound as a colorless crystal.

b) Preparation of N-Benzyloxycarbonyl-L-leucine-(1-hydroxymethyl-2-methyl)butylamide:

In 100 ml of t-butanol were suspended 9.4 g of N-benzyloxycarbonyl-L-leucine-L-isoleucine methyl ester obtained in (a) above and 900 mg of sodium borohydride, followed by refluxing at 90° C. in a nitrogen atmosphere. Then, 20 ml of absolute methanol was added thereto dropwise while refluxing. After the addition, the reaction mixture was further refluxed with stirring for 3 hours, followed by cooling to room temperature. To the reaction mixture was added 300 ml of water under cooling with ice, and the methanol and t-butanol were removed by distillation under reduced pressure. The residue was extracted three times with ethyl acetate, and the extract was washed with a saturated brine and dried over anhydrous sodium sulfate. The solvent was removed by distillation under reduced pressure, and the residue was purified by medium-pressure column chromatography on silica gel to obtain 3.0 g of the titled compound as a colorless crystal.

c) Preparation of N-Benzyloxycarbonyl-L-leucine-(1-formyl-2-methyl)butylamide:

In 20 ml of anhydrous DMSO were dissolved 2.8 g of N-benzyloxycarbonyl-L-leucine-(1-hydroxymethyl-2-methyl)butylamide obtained in (b) above and 3.2 ml of triethylamine, and a solution of 3.7 g of a sulfur trioxidepyridine complex in 10 ml of anhydrous DMSO was added thereto while stirring. After stirring at room temperature for 10 minutes, the reaction mixture was poured into 100 ml of ice-water and extracted three times with ethyl acetate. The extract was washed successively with a 10% citric acid solution, a saturated brine, a saturated sodium bicarbonate solution, and a saturated brine and dried over anhydrous sodium sulfate. The solvent was removed by distillation under reduced pressure, and the residue was crystallized from a mixed solvent of ethyl acetate and hexane to obtain 2.2 g of the titled compound as a colorless crystal.

EXAMPLE 36

Preparation of N-Acetyl-L-leucine-(1-dimethoxymethyl-2-methyl)-butylamide a) Preparation of N-Benzyloxycarbonyl-L-leucine-(1-dimethoxymethyl-2-methyl)butylamide:

In 20 ml of methanol was dissolved 2.2 g of N-benzyloxycarbonyl-L-leucine-(1-formyl-2-methyl)butylamide obtained in the same manner as in Example 35, and a catalytic amount of p-toluenesulfonic acid was added thereto, followed by stirring at room temperature for 8 hours. After completion of the reaction, the solvent was removed by distillation under reduced pressure, and the residue was partitioned between water and an ethyl acetate. The organic layer was washed with a saturated sodium bicarbonate solution and then with a saturated brine and dried over anhydrous sodlum sulfate. The solvent was removed by distillation under reduced pressure, and the residue was purified by medium-pressure column chromatography on silica gel to obtain 2.2 g of the titled compound as a colorless crystal.

b) Preparation of N-Acetyl-L-leucine-(1-dimethoxymethyl-2-methyl)butylamide:

In 50 ml of ethanol was dissolved 2.0 g of N-benzyloxycarbonyl-L-leucine-(1-dimethoxymethyl-2-methyl)butylamide obtained in (a) above, and a catalytic amount of palladium-on-carbon was added thereto. The mixture was allowed to react at room temperature for 12 hours in a hydrogen atmosphere. After completion of the hydrogenation reaction, the catalyst was removed by filtration, and the solvent was removed by distillation under reduced pressure. The residue was dissolved in 50 ml of methylene chloride, and 3 m@ of pyridine and 3 ml of acetic anhydride were added thereto, followed by stirring at room temperature for 4 hours. Water was added to the reaction mixture, and the organic layer was washed successively with a 10% citric acid solution, a saturated brine, a saturated sodium bicarbonate solution, and a saturated brine and dried over anhydrous sodium sulfate. The solvent was removed by distillation under reduced pressure, and the residue was crystallized from a mixed solvent of ethyl acetate and hexane to obtain 1.0 g of the titled compound as a colorless crystal.

EXAMPLE 37

Preparation of N-Acetyl-L-leucine-(1-di-n-propyloxymethyl)pentylamide

In 10 ml of n-propanol was dissolved 1 g of N-acetyl-L-leucine-(1-formyl)pentylamide obtained in the same manner as in Example 16-(c), and 0.8 ml of boron trifluoride ethyl etherate was added thereto, and the mixture was allowed to react at room temperature for 24 hours. After completion of the reaction, the solvent was removed by distillation under reduced pressure, and the residue was purified by medium-pressure column chromatography on silica gel to obtain 340 mg of the titled compound as a colorless crystal.

EXAMPLE 38

Preparation of
N-Acetyl-L-leucine-(1-di-n-butoxymethyl)pentylamide

In 10 ml of n-butanol was dissolved 1 g of N-acetyl-L-leucine-(1-formyl)pentylamide obtained in the same manner as in Example 16-(c), and 0.8 ml of boron trifluoride ethyl etherate was added thereto, and the mixture was allowed to react at room temperature for 24 hours. After completion of the reaction, the solvent was removed by distillation under reduced pressure, and the residue was purified by medium-pressure column chromatography on silica gel to obtain 460 mg of the titled compound as a colorless crystal.

EXAMPLE 39

Preparation of
N-Benzyloxycarbonyl-L-leucine-(1-diethoxymethyl)-pentylamide

In 10 ml of ethanol was dissolved 1 g of N-benzyloxycarbonyl-L-leucine-(1-formyl)pentylamide obtained in the same manner as in Example 4-(b), and a catalytic amount of p-toluenesulfonic acid was added thereto. The mixture was allowed to react at room temperature for 4 hours. After completion of the reaction, the solvent was removed by distillation under reduced pressure, and the residue was purified by medium-pressure column chromatography on silica gel to obtain 1 g of the titled compound as a colorless crystal.

EXAMPLE 40

Preparation of
N-Benzyloxycarbonyl-L-phenylalanine-(1-formyl)pentylamide a) Preparation of N-Benzyloxycarbonyl-L-phenylalanyl-L-norleucine Methyl Ester:

In 50 ml of methylene chloride was dissolved 1.8 g of L-norleucine methyl ester hydrochloride, and 1.1 ml of N-methylmorpholine was added to the solution. To the solution were further added 3.0 g of N-benzyloxycarbonyl-L-phenylalanine and 1.9 g of 1-ethyl-3-(3-diethylaminopropyl)carbodiimide, and the mixture was stirred at room temperature for 24 hours. After completion of the reaction, water was added to the reaction mixture, and the mixture was extracted with ethyl acetate. The organic layer was washed successively with a 10% citric acid solution, a saturated brine, a saturated sodium bicarbonate solution, and a saturated brine and dried over sodium sulfate. The solvent was removed by distillation under reduced pressure to obtain 4.1 g of the titled compound.

b) Preparation of N-Benzyloxycarbonyl-L-phenylalanine-(1-hydroxymethyl)pentylamide:

In 90 ml of t-butanol were suspended 4.1 g of N-benzyloxycarbonyl-L-phenylalanyl-L-norleucine methyl ester obtained in (a) above and 390 mg of sodium borohydride, and the suspension was refluxed at 80° C. To the suspension was added dropwise 18 ml of absolute methanol under refluxing. After the addition, the mixture was further refluxed for 3 hours and cooled to room temperature. To the reaction mixture was added 100 ml of water under ice-cooling, and the solvent was removed by distillation under reduced pressure. The residual aqueous layer was extracted with ethyl acetate, and the organic layer was washed with a saturated brine and dried over anhydrous sodium sulfate. The solvent was removed by distillation under reduced pressure, and the residue was purified by medium-pressure column chromatography on silica gel to obtain 2 g of the titled compound as a colorless crystal.

c) Preparation of N-Benzyloxycarbonyl-L-phenylalanine-(1-formyl)pentylamide:

In 10 ml of anhydrous DMSO were dissolved 1.5 g of N-benzyloxycarbonyl-L-phenylalanine-(1-hydroxymethyl)pentylamide obtained in (b) above and 2.1 ml of triethylamine, and a solution of 2.4 g of sulfur trioxide-pyridine complex in 10 ml of anhydrous DMSO was added thereto while stirring. After stirring at room temperature for 10 minutes, the reaction mixture was poured into 200 ml of ice-water and extracted with ethyl acetate. The organic layer was washed successively with a 10% citric acid solution, a saturated brine, a saturated sodium bicarbonate solution, and a saturated brine and dried over anhydrous sodium sulfate. The solvent was removed by distillation under reduced pressure, and the residue was purified by medium-pressure column chromatography on silica gel to obtain 1.0 g of the titled compound as a colorless crystal.

EXAMPLE 41

Preparation of
N-Benzyloxycarbonyl-L-phenylalanine-(1-diethoxymethyl)pentylamide In 10 ml of ethanol was dissolved 1.0 g of N-benzyloxycarbonyl-L-phenylalanine-(1-formyl)pentylamide obtained in the same manner as in Example 40-(c), and a catalytic amount of p-toluenesulfonic aeld was added thereto. The mixture was allowed to react at room temperature for 12 hours. After completion of the reaction, the solvent was removed by distillation under reduced pressure. Water was added to the residue, followed by filtration to recover 1.0 g of the titled compound as a colorless crystal.

The structural formula and physical properties of each product prepared in Examples 1 to 41 are shown in Table 1 below.

TABLE 1

| Example No. | Chemical Structure | Characterized Form (m.p. °C) | $^1$H-NMR (δ-ppm, TMS standard) |
|---|---|---|---|
| 1 | Cbz-Leu-NH-CH(nBu)-C(O)-CH2-C(O)-O-Et | oil | 0.80–0.92(9H, m), 1.20–2.00(12H, m), 4.10–4.40(3H, m), 5.80(2H, s), 5.28–5.36(1H, m), 6.66–6.86(1H, m), 7.29(5H, s). (solvent: CDCl$_3$) |
| 2 | Cbz-Leu-NH-CH(nBu)-C(O)-CH3 | colorless crystal (78–79) | 0.80–0.95(9H, m), 1.20–1.80(9H, m), 2.18(3H, s), 4.05–4.28(1H, m), 4.46–4.64(1H, m), 5.08(2H, s), 6.48–6.58(1H, m), 7.31(5H, s). (solvent: CDCl$_3$) |
| 3 | Cbz-Leu-NH-CH(nBu)-C(O)-CH2-Br | colorless crystal (106–107) | 0.80–0.95(9H, m), 1.20–2.00(9H, m), 4.00(2H, s), 4.04–4.26(1H, m), 4.64–4.84(1H, m), 5.10(2H, s), 6.44–6.52(1H, m), 7.32(5H, s). (solvent: CDCl$_3$) |
| 4 | Cbz-Leu-NH-CH(nBu)-CH(OH)-CF2-C(O)-O-Et | oil | 0.80–1.90(18H, m), 1.34(3H, t, J=9Hz), 3.95–4.28(2H, m), 4.32(2H, q, J=9Hz), 5.10(2H, s), 5.22(1H, d, J=10Hz), 5.30(1H, m), 6.63(1H, d, J=10Hz), 7.33(5H, m). (solvent: CDCl$_3$) |
| 5 | Cbz-Leu-NH-CH(nBu)-CH(OH)-CH2-C(O)-O-Et | oil | 0.80–2.30(18H, m), 1.20(3H, t, J=9Hz), 3.90–4.50(3H, m), 4.15(2H, q, J=9Hz), 4.55(1H, m), 5.10(1H, s), 5.12(1H, s), 5.20(1H, d, J=7Hz), 5.35(1H, d, J=7Hz), 7.25–7.30(5H, m). (solvent: CDCl$_3$) |
| 6 | Cbz-Leu-NH-CH(nBu)-C(O)-CH2-C(O)-O-Et | colorless crystal (60–63) | 0.80–2.00(18H, m), 1.28(3H, t, J=7.5Hz), 3.52(2H, m), 4.19(2H, q, J=7.5Hz), 4.20(1H, m), 5.10(2H, s), 5.11(1H, m), 6.62(1H, dd, J=9Hz, J=15Hz), 7.32(5H, m). (solvent: CDCl$_3$) |

TABLE 1-continued

| Example No. | Chemical Structure | Characterized Form (m.p. °C) | $^1$H-NMR (δ-ppm, TMS standard) |
|---|---|---|---|
| 7 | (Cbz-Leu-NH-CH(nBu)-CH(OMe)$_2$) | colorless crystal (95–96) | 0.80–1.75(18H, m), 3.38(3H, s), 3.40(3H, s), 4.10(3H, m), 5.10(2H, s), 5.14(1H, m), 5.89(1H, d, J=12Hz), 7.34(5H, m). (solvent: CDCl$_3$) |
| 8 | (Cbz-Leu-NH-CH(nBu)-CH=N-NH-C(O)NH$_2$) | colorless crystal (120–122) | 0.80–1.75(18H, m), 4.20(2H, m), 4.56(1H, s), 5.11(2H, s), 5.18(1H, m), 6.81(1H, m), 7.03(1H, s), 7.32(5H, s), 9.12(2H, s). (solvent: CDCl$_3$) |
| 9 | (Cbz-Leu-NH-CH(nBu)-CH(1,3-dioxolane)) | colorless crystal (95–97) | 0.80–2.20(18H, m), 3.90(4H, m), 4.20(2H, m), 4.83(1H, m), 5.10(2H, s), 5.32(1H, d, J=12Hz), 6.02(1H, d, J=12Hz), 7.30–7.36(5H, m). (solvent: CDCl$_3$) |
| 10 | (Cbz-Leu-NH-CH(nBu)-benzimidazole) | colorless crystal (78–80) | 0.50–2.23(18H, m), 4.37(1H, m), 5.08(2H, s), 5.19(1H, m), 6.00(1H, d, J=10Hz), 7.20(9H, m), 7.50(1H, s), 8.36(1H, m). (solvent: CDCl$_3$) |
| 11 | (Cbz-Leu-NH-CH(nBu)-CH=N-OH) | colorless crystal (146–147) | 0.80–1.80(18H, m), 4.00–4.65(3H, m), 5.10(2H, s), 5.46(1H, d, J=9Hz), 5.70(1H, d, J=9Hz), 6.62(1H, s), 7.34(5H, m). (solvent: CDCl$_3$) |
| 12 | (Cbz-Leu-NH-CH(nBu)-CH(OAc)$_2$) | oil | 0.80–1.90(18H, m), 2.09(3H, s), 2.10(3H, s), 3.85–4.00(2H, m), 4.55(1H, m), 5.10(2H, s), 5.23(1H, m), 6.60(1H, d, J=6Hz), 7.28(5H, m). (solvent: CDCl$_3$) |

TABLE 1-continued

| Example No. | Chemical Structure | Characterized Form (m.p. °C.) | ¹H-NMR (δ-ppm, TMS standard) |
|---|---|---|---|
| 13 | (structure) | colorless crystal (120–121) | 0.80–0.95(9H, m), 1.18–1.80(9H, m), 3.12(4H, s), 4.00–4.26(2H, m), 4.66(1H, d, J=5Hz), 5.08(2H, s), 5.28(1H, d, J=8Hz), 6.24(1H, d, J=10Hz). (solvent: CDCl$_3$) |
| 14 | (structure) | colorless crystal (130–131) | 0.86–0.96(9H, m), 1.20–2.20(11H, m), 2.76–2.92(4H, m), 4.02–4.30(3H, m), 5.08(2H, s), 6.06–6.15(1H, m), 7.30(5H, s). (solvent: CDCl$_3$) |
| 15 | (structure) | colorless crystal (142–143) | 0.80–1.80(18H, m), 2.02(3H, s), 2.56–4.64(7H, m), 6.10–6.52(3H, m). (solvent: CDCl) |
| 16 | (structure) | colorless crystal (125–126) | 0.70–1.80(18H, m), 1.98(3H, s), 3.36(3H, s), 3.40(3H, s), 3.80–4.50(3H, m), 5.90(2H, m). (solvent: CDCl$_3$) |
| 17 | (structure) | colorless crystal (118–119) | 0.70–1.80(18H, m), 1.98(3H, s), 3.90(4H, m), 4.00–4.82(3H, m), 5.96(2H, m). (solvent: CDCl$_3$) |
| 18 | (structure) | colorless crystal (148–150) | 0.80–1.80(18H, m), 2.07(1.5H, s), 2.09(1.5H, s), 4.40–4.60(3H, s). (solvent: CDCl$_3$) |

TABLE 1-continued

| Example No. | Chemical Structure | Characterized Form (m.p. °C.) | $^1$H-NMR (δ-ppm, TMS standard) |
|---|---|---|---|
| 19 | 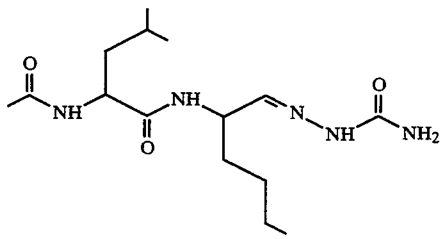 | colorless crystal (92–94) | 0.80–2.20(18H, m), 2.04(3H, s), 4.00–4.60(3H, m), 6.20–6.44(1H, m), 7.10–7.40(2H, m), 9.00(1H, m). (solvent: CDCl$_3$) |
| 20 | 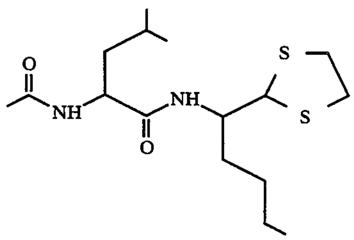 | colorless crystal (142–144) | 0.80–0.96(9H, m), 1.20–1.80(9H, m), 1.98(3H, s), 3.18(4H, s), 4.00–4.22(1H, m), 4.32–4.56(1H, m), 4.66(1H, d, J=4Hz), 6.18–6.40(2H, m). (solvent: CDCl$_3$) |
| 21 | 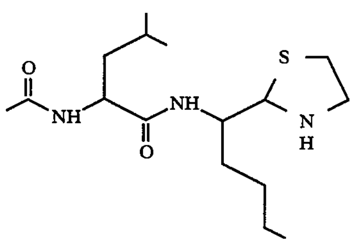 | colorless crystal (142–143) | 0.80–1.80(18H, m), 2.02(3H, s), 2.56–4.64(7H, m), 6.10–6.52(3H, m). (solvent: CDCl$_3$) |
| 22 | 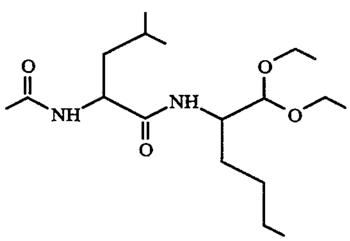 | colorless crystal (128–129) | 0.80–1.80(18H, m), 1.98(3H, s), 3.38–3.78(4H, m), 4.32(1H, d, J=4Hz), 4.00(1H, m), 4.40(1H, m), 6.14(1H, d, J=9Hz), 6.48(1H, d, J=8Hz). (solvent: CDCl$_3$) |
| 23 | 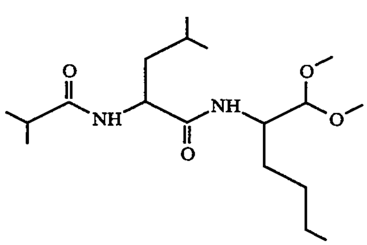 | colorless crystal (139–141) | 0.80–2.00(18H, m), 1.12(3H, d, J=7Hz), 1.20(3H, d, J=7Hz), 2.38(1H, dq, J=7Hz, J=7Hz), 3.40(3H, s), 3.42(3H, s), 3.84–4.50(3H, m), 5.98(2H, m). (solvent: CDCl$_3$) |
| 24 | 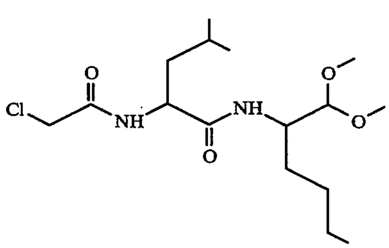 | colorless crystal (127–128) | 0.70–1.80(18H, m), 3.40(3H, s), 3.44(3H, s), 3.80–4.55(3H, m), 4.05(2H, s), 5.82(1H, d, J=8Hz), 6.95(1H, d). (solvent: CDCl$_3$) |

TABLE 1-continued

| Example No. | Chemical Structure | Characterized Form (m.p. °C.) | $^1$H-NMR (δ-ppm, TMS standard) |
|---|---|---|---|
| 25 | 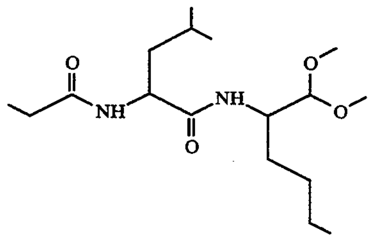 | colorless crystal (148–150) | 0.75–1.80(18H, m), 1.16(3H, t, J=7Hz), 2.24(2H, q, J=7Hz), 3.40(3H, s), 3.44(3H, s), 3.80–4.60(3H, m), 5.92(2H, m). (solvent: CDCl$_3$) |
| 26 | 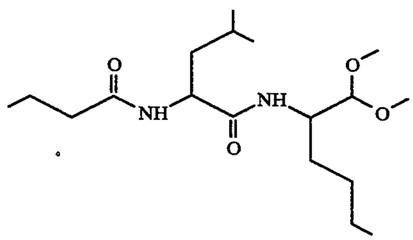 | colorless crystal (162–164) | 0.70–1.90(18H, m), 0.96(3H, t, J=7.5Hz), 1.60(2H, m), 2.20(2H, t, J=7.5Hz), 3.40(3H, s), 3.44(3H, s), 3.85–4.65(3H, m), 5.95(2H, m). (solvent: CDCl$_3$) |
| 27 | 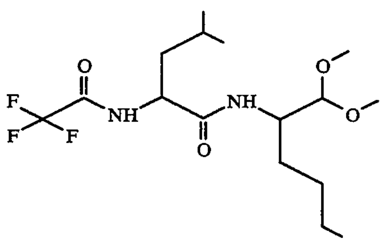 | colorless crystal (140–142) | 0.70–1.80(18H, m), 3.40(3H, s), 3.42(3H, s), 3.80–4.60(3H, m), 5.80(1H, m), 7.08(1H, m). (solvent: CDCl$_3$) |
| 28 | 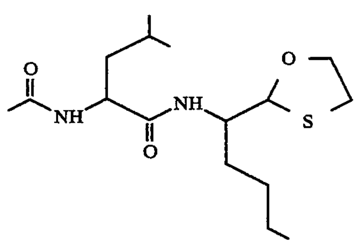 | colorless crystal (119–121) | 0.80–0.96(9H, m), 1.20–1.80(9H, m), 2.00(3H, s), 2.84–3.02(2H, m), 3.60–3.88(1H, m), 3.98–4.52(3H, m), 5.13(1H, m), 5.96–6.20(2H, m). (solvent: CDCl$_3$) |
| 29 | 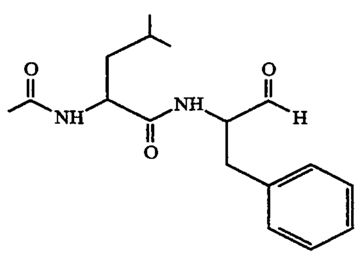 | white powder | 0.88(6H, t, J=5.5Hz), 1.30–2.24(3H, m), 1.94(3H, s), 3.08(2H, m), 4.20–4.90(2H, m), 6.04(1H, t, J=8Hz), 6.88(1H, m), 7.20(5H, m), 9.58(1H, s). (solvent: CDCl$_3$) |
| 30 | 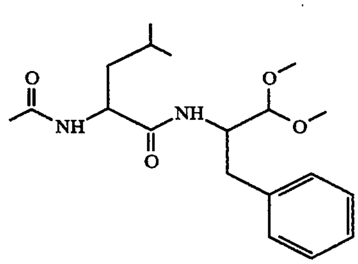 | colorless crystal (125–126) | 0.94(6H, d, J=6Hz), 1.10–1.80(3H, m), 1.94(3H, s), 2.88(2H, m), 3.40(3H, s), 3.46(3H, s), 4.05–4.60(3H, m), 5.75(1H, d, J=8Hz), 6.17(1H, d, J=9Hz), 7.00–7.40(5H, m). (solvent: CDCl$_3$) |

TABLE 1-continued

| Example No. | Chemical Structure | Characterized Form (m.p. °C.) | ¹H-NMR (δ-ppm, TMS standard) |
|---|---|---|---|
| 31 | 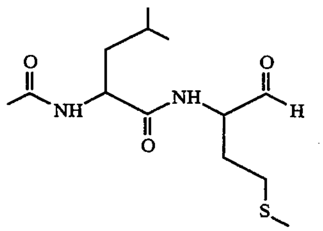 | oil | 0.94(6H, d, J=4Hz), 1.16–2.34(5H, m), 2.00(3H, s), 2.06(3H, s), 2.40–2.60(2H, m), 4.40–4.60(2H, m), 5.97(1H, broad d), 5.90–7.12(1H, m), 9.56(1H, s). (solvent: CDCl₃) |
| 32 | 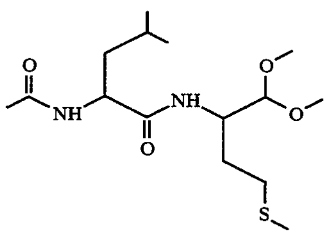 | colorless crystal (120–122) | 0.94(6H, d, J=5Hz), 1.66–1.86(5H, m), 2.00(3H, s), 2.08(3H, s), 2.40–2.56(2H, m), 3.39(3H, s), 3.41(3H, s), 4.10–4.50(3H, m), 5.96(1H, m), 6.10(1H, m). (solvent: CDCl₃) |
| 33 | 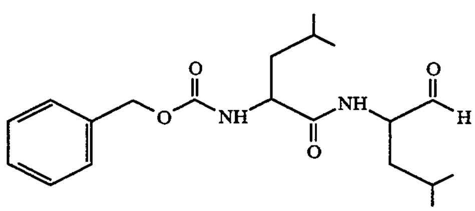 | colorless crystal (140–142) | 0.70–1.20(12H, m), 1.20–1.90(6H, m), 4.20(1H, m), 4.48(1H, m), 5.40(2H, s), 5.60(1H, d, J=7Hz), 6.40(1H, d, J=7Hz), 7.32(5H, s), 9.50(1H, s). (solvent: CDCl₃) |
| 34 | 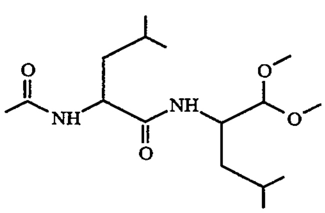 | colorless crystal (149–150) | 0.94(12H, t, J=5Hz), 1.20–1.80(6H, m), 2.00(3H, s), 3.40(3H, s), 3.43(3H, s), 3.80–4.50(3H, m), 6.00(2H, t, J=9Hz). (solvent: CDCl₃) |
| 35 | 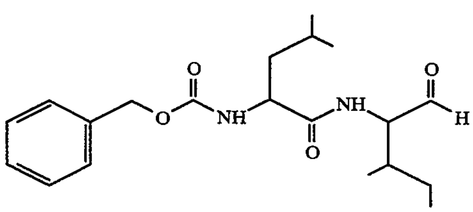 | oil | 0.80–1.00(12H, m), 1.14–2.18(6H, m), 4.10–4.30(1H, m), 4.48–4.70(1H, m), 5.08(2H, s), 6.50–6.56(1H, m), 7.30(5H, s), 9.60(1H, s). (solvent: CDCl₃) |
| 36 | 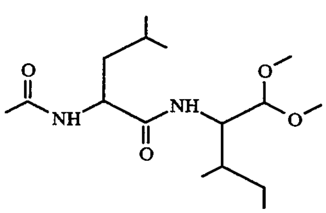 | colorless crystal (145–147) | 0.86–0.96(12H, m), 1.40–1.80(6H, m), 1.98(3H, s), 3.32, 3.38(each 3H, both s), 3.84–4.04(1H, m), 4.28(1H, d, J=4Hz), 4.36–4.52(1H, m), 6.06(2H, d, J=8Hz). (solvent: CDCl₃) |

TABLE 1-continued

| Example No. | Chemical Structure | Characterized Form (m.p. °C.) | $^1$H-NMR (δ-ppm, TMS standard) |
|---|---|---|---|
| 37 | 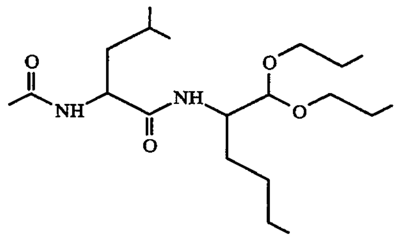 | colorless crystal (114–116) | 0.87–0.96(15H, m), 1.28–1.82(13H, m), 2.00(3H, s), 3.24–3.73(4H, m), 3.92–4.14(1H, m), 4.29–4.52(2H, m), 5.90–6.06(2H, m). (solvent: CDCl$_3$) |
| 38 | 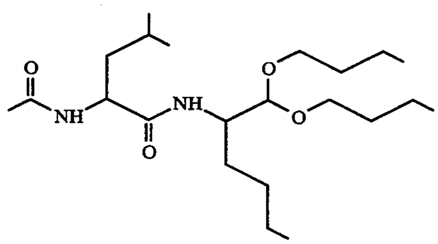 | colorless crystal (94–96) | 0.90–0.96(15H, m), 1.26–1.84(17H, m), 1.98(3H, s), 3.07–3.86(4H, m), 3.90–4.10(1H, m), 4.29(1H, d, J=3Hz), 4.27–4.52(1H, m), 5.86–6.02(2H, m). (solvent: CDCl$_3$) |
| 39 | 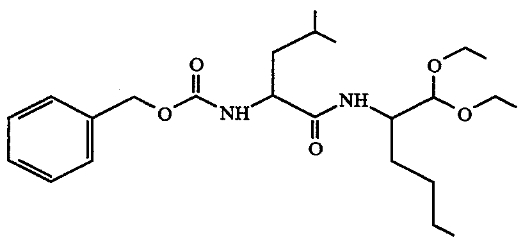 | colorless crystal (94–96) | 0.80–0.96(9H, m), 1.16(3H, t, J=7Hz), 1.18(3H, t, J=7Hz), 1.20–1.74(9H, m), 3.36–3.78(4H, m), 3.92–4.16(2H, m), 4.32(1H, d, J=4Hz), 5.08(2H, s), 5.00–5.24(1H, m), 5.90(1H, m), 7.11(5H, s). (solvent: CDCl$_3$) |
| 40 | 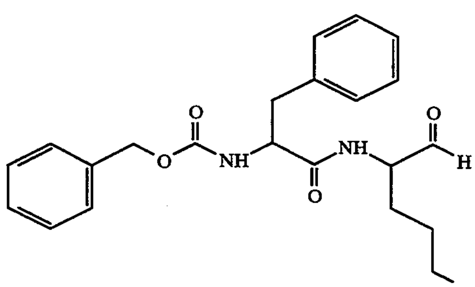 | colorless crystal (136–138) | 0.85(3H, m), 1.16–1.88(6H, m), 3.03–3.15(2H, m), 4.28–4.55(2H, m), 5.08(2H, s), 5.24(1H, m), 6.18(1H, m), 7.22(5H, s), 7.30(5H, s), 9.38(1H, s). (solvent: CDCl$_3$) |
| 41 | 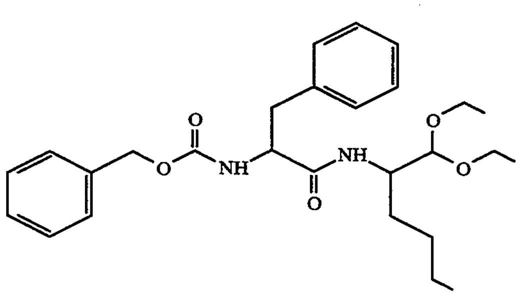 | colorless crystal (104–106) | 0.84(3H, m), 1.04–1.60(12H, m), 3.03–3.10(2H, m), 3.20–3.70(4H, m), 4.14(1H, d, J=4Hz), 4.26–4.48(2H, m), 5.06(2H, s), 5.12(1H, m), 5.80(1H, m), 5.23(5H, s), 5.30(5H, s). (solvent: CDCl$_3$) |

TEST EXAMPLE 1

Effect on PTHrp(1–34)-Induced Hypercalcemia in Rats (p.o.)

Some of the compounds shown in Table 1 were orally administered to 5-week-old male Wistar rats weighing from 9 to 110 g (5 animals per group) at a dose of 40 mg/kg body weight. Four hours later, 5 nmole/kg of PTHrp(1–34) was intravenously injected into the animals. One hour after the administration of PTHrp(1–34)sequence ID No. 1, a blood sample was collected from each rat, and the blood calcium concentration was determined by the octocresolphthalein complexone method. The results obtained are shown in Table 2.

TABLE 2

Effect on Hypercalcemia (p.o.)

| Group | PTHrp-Treatment | Test Compound | Dose (mg/kg) | Ca Conc. ± S.E. (mg/dl) |
|---|---|---|---|---|
| 1 | yes | — | 0 | 10.84 ± 0.11 |
| 2 | yes | Example 7 | 40 | 10.36 ± 0.11* |
| 3 | yes | Example 9 | 40 | 10.41 ± 0.08* |
| 4 | yes | Example 15 | 40 | 9.98 ± 0.13** |
| 5 | yes | Example 16 | 40 | 9.91 ± 0.13** |
| 6 | yes | Example 17 | 40 | 9.97 ± 0.17** |
| 7 | yes | Example 18 | 40 | 10.36 ± 0.12* |
| 8 | yes | Example 19 | 40 | 10.14 ± 0.08** |
| 9 | yes | Example 21 | 40 | 9.98 ± 0.10** |
| 10 | yes | Example 22 | 40 | 10.05 ± 0.13** |
| 11 | yes | Example 23 | 40 | 9.83 ± 0.13** |
| 12 | yes | Example 24 | 40 | 10.12 ± 0.09** |
| 13 | yes | Example 25 | 40 | 9.88 ± 0.09** |
| 14 | yes | Example 26 | 40 | 9.85 ± 0.08** |
| 15 | yes | Example 27 | 40 | 9.91 ± 0.13** |
| 16 | yes | Example 33 | 40 | 10.26 ± 0.13** |

Note: Average blood calcium concentration ± S.E. (n = 5)
*: $P < 0.05$ vs. Ca concentration of Group 1.
**: $P < 0.01$ vs. Ca concentration of Group 1.

TEST EXAMPLE 2

Effect on PTHrp(1-34)-Induced Hypercalcemia in Rats (i.p.)

Some of the compounds shown in Table 1 were intraperitoneally administered to 5-week-old male Wistar rats each weighing 90 to 110 g (5 animals per group) at a dose of 40 mg/kg body weight. Two hours later, 5 nmole/kg of PTHrp(1-34) was intravenously injected. One hour after the administration of PTHrp(1-34), a blood sample was collected from each animal, and the blood calcium concentration was determined according to the same method as in Test Example 1. The results obtained are shown in Table 3.

TABLE 3

Effect on Hypercalcemia (i.p.)

| Group | PTHrp-Treatment | Test Compound | Dose (mg/kg) | Ca Conc. ± S.E. (mg/dl) |
|---|---|---|---|---|
| 1 | yes | — | 0 | 10.79 ± 0.13 |
| 2 | yes | Example 1 | 40 | 10.33 ± 0.12* |
| 3 | yes | Example 7 | 40 | 10.29 ± 0.14* |
| 4 | yes | Example 12 | 40 | 10.27 ± 0.08** |
| 5 | yes | Example 13 | 40 | 10.23 ± 0.05** |
| 6 | yes | Example 15 | 40 | 10.13 ± 0.21* |
| 7 | yes | Example 16 | 40 | 9.95 ± 0.14** |
| 8 | yes | Example 17 | 40 | 10.16 ± 0.05** |
| 9 | yes | Example 21 | 40 | 9.96 ± 0.07** |
| 10 | yes | Example 22 | 40 | 9.67 ± 0.18** |

Note: Average blood calcium concentration ± S.E. (n = 5)
*: $P < 0.05$ vs. Ca concentration of Group 1.
**: $P < 0.01$ vs. Ca concentration of Group 1.

As is shown in Tables 2 and 3, the compounds according to the present invention significantly suppressed the increase in blood calcium concentration either in oral or intraperitoneal administration. These results suggest that the compounds of the present invention are effective in preventing or inhibiting malignant humoral hypercalcemia and prove that the compounds of the present invention are useful as a prophylactic or therapeutic agent for bone diseases.

Preparation of Tablets

| | |
|---|---|
| Compound of Example 7 | 100.0 g |
| Microcrystalline cellulose | 22.5 g |
| Magnesium stearate | 2.5 g |
| | Total: 125.0 g |

The above ingredients were mixed together and punched into tablets by means of a single-shot tableting machine to prepare tablets each having a diameter of 9 mm, weighing 250 mg, and containing 200 mg of the compound of Example 7.

Preparation of Granules

| | |
|---|---|
| Compound of Example | 30 g |
| Lactose | 265 g |
| Magnesium stearate | 5 g |
| | Total: 300 g |

The above ingredients were thoroughly mixed together. The mixture was compression molded, ground, regulated, and sifted to obtain satisfactory granules of 20 to 50 mesh containing 10% active ingredient.

Preparation of Capsules

| | |
|---|---|
| Compound of Example 23 | 100 (parts by weight) |
| Potato starch | 148 (by weight) |
| Magnesium stearate | 2 (by weight) |
| | Total: 250 (by weight) |

The above ingredients were thoroughly mixed in a grinder and filled in No. 1 hard gelatin capsules in 250 mg portions to obtain capsules each containing 100 mg of the compound of Example 23.

FORMULATION EXAMPLE 4

Preparation of Rectal Suppositories

Witepsol H-15 (produced by Dynamic Nobel) was melted by heat, and the compound of Example 7 was added thereto so as to give a concentration of 12.5 mg/ml. After being uniformly mixed, the mixture was injected into a rectal suppository mold in 2 ml portions and cooled to obtain rectal suppositories each containing 25 mg of the compound of Example 7.

The active ingredient according to the present invention is capable of preventing or inhibiting malignant humoral hypercalcemia and secondary hyperparathyroidism and is thus useful as a prophylactic or therapeutic agent for bone diseases.

What is claimed is:

1. A pharmaceutical compostion for inhibiting loss of calcium from bones wherein said composition contains an effective amount of a dipeptide derivative represented by the formula (I):

$$R^1NH\text{---}CH(R^2)\text{---}CO\text{---}NH\text{---}CH(R^3)\text{---}R^4 \quad (I)$$

wherein $R^1$ represents an aliphatic acyl group, a halogen-substituted aliphatic acyl group, or benzyloxycarbonyl group;

$R^2$ represents a lower alkyl group or an aralkyl group;
$R^3$ represents a lower alkyl group, an aralkyl group, or methylthioethyl group; and
$R^4$ represents an aliphatic acyl group substituted with a lower alkoxycarbonyl group, or $R_4$ represents a di-lower alkoxymethyl group, a 1-hydroxy-2-lower alkoxycarbonylethyl group, a halogen-substituted 1-hydroxy-2-lower alkoxycarbonylethyl group, hydroxyiminomethyl group, ureidoiminomethyl group, benzimidazol-2-yl group, or a group:

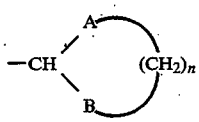

wherein A and B, which may be the same or different, each represents O, S, NH; and n represents 2 or 3;
as an active ingredient together with a pharmaceutically acceptable carrier or adjuvant.

2. The pharmaceutical composition of claim 1 wherein the active ingredient is N-acetyl-L-leucine-(1-diethoxymethyl)-pentylamide.

3. A dipeptide derivative represented by the formula (I):

$$R^1NH\text{---}CH(R^2)\text{---}CO\text{---}NH\text{---}CH(R^3)\text{---}R^4 \quad (I)$$

wherein R represents an aliphatic acyl group, a halogen-substituted aliphatic acyl group, or benzyloxycarbonyl group;

$R^2$ represents a lower alkyl group or an aralkyl group;
$R^3$ represents a lower alkyl group, or an aralkyl group, or methylthioethyl group; and $R^4$ represents an aliphatic acyl group substituted with a lower alkoxycarbonyl group, or $R_4$ represents a di-lower alkoxymethyl group, a diacyloxymethyl group, a 1-hydroxy-2-lower alkoxycarbonylethyl group, a halogen-substituted 1-hydroxy-2-lower alkoxycarbonylethyl group, hydroxyiminomethyl group, ureidoiminomethyl group, benzimidazol-2-yl group, or a group:

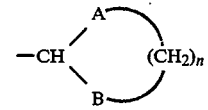

wherein A and B, which may be the same or different, each represents O, S, NH; and n represents 2 or 3.

4. A dipeptide derivative as claimed in claim 3, wherein the lower alkyl group as $R^2$ is an isobutyl group and the lower alkyl group as $R^3$ is an n-butyl group.

5. A dipeptide derivative as claimed in claim 3, wherein $R^1$ is an acetyl group, propanoyl group, n-butanoyl group, isobutanoyl group or benzyloxycarbonyl group, $R^2$ is an isobutyl group, $R^3$ is an n-butyl group and $R^4$ is a dimethoxymethyl group, diethoxymethyl group, 1,3-dioxolan-2-yl group, or thiazolidine-2-yl group.

6. A dipeptide derivative, according to claim 3, of the following formula:

N-acetyl-L-leucine-(1-diethoxymethyl)-pentylamide.

7. A method of inhibiting loss of calcium from the bones [preventing or treating a bone resorption disease selected from malignant hypercalcemia, bone Paget's disease and osteoporosis] comprising administering to a patient in need of same an effective amount of a dipeptide represented by the formula (I):

$$R^1NH\text{---}CH(R^2)\text{---}CO\text{---}NH\text{---}CH(R^3)\text{---}R^4 \quad (I)$$

wherein $R^1$ represents an aliphatic acyl group, a halogen-substituted aliphatic acyl group. or benzyloxycarbonyl group;

$R^2$ represents a lower alkyl group or an aralkyl group;
$R^3$ represents a lower alkyl group, or an aralkyl group, or methylthioethyl group; and $R^4$ represents an aliphatic acyl group substituted with a lower alkoxycarbonyl group, or $R_4$ represents a dilower alkoxymethyl group, a 1-hydroxy-2-lower alkoxycarbonylethyl group, a halogen-substituted 1-hydroxy-2-lower alkoxycarbonylethyl group, hydroxyiminomethyl group, ureidoiminomethyl group, benzimidazol-2-yl group, or a group:

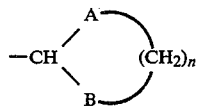

wherein A and B, which may be the same or different, each represents O, S, NH; and n represents 2 or 3.

8. A method according to claim 7 wherein the lower alkyl group as $R^2$ is an isobutyl group and the lower alkyl group as $R^3$ is an n-butyl group.

9. The method according to claim 7, wherein $R^1$ is an acetyl group, propanoyl group, n-butanoyl group, isobutanoyl group or benzyloxycarbonyl group, $R^2$ is an isobutyl group, $R^3$ is an n-butyl group and $R^4$ is a dimethoxymethyl group, diethoxymethyl group, 1-bromoacetyl group, 1,3-dioxolan-2-yl group, or thiazolidine-2-yl group.

10. The method of claim 7 wherein the compound administered is N-acetyl-L-leucine-(1-diethoxymethyl)-pentylamide.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:

(A) LENGTH: 34 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (ix) FEATURE:
(A) NAME/KEY: Peptide
(B) LOCATION: 1..34

(xi) SEQUENCE DESCRIPTION: SEQ ID NO:1:

```
Ala Val Ser Glu His Gln Leu Leu His Asp Lys Gly Lys Ser Ile Gln
1               5                   10                  15
Asp Leu Arg Arg Arg Phe Phe Leu His His Leu Ile Ala Glu Ile His
            20                  25                  30
Thr Ala
```